United States Patent
Ohta et al.

(10) Patent No.: US 7,253,269 B1
(45) Date of Patent: Aug. 7, 2007

(54) **MODIFIED CDNA OF RAT *BCL-X* GENE AND MODIFIED PROTEIN**

(75) Inventors: Shigeo Ohta, Tokyo (JP); Sadamitsu Asoh, Kanagawa (JP)

(73) Assignee: Japan Science and Technology Corporation, Saitama (JP)

( * ) Notice: Subject to any disclaimer, the term of this patent is extended or adjusted under 35 U.S.C. 154(b) by 677 days.

(21) Appl. No.: 10/049,822

(22) PCT Filed: Aug. 17, 2000

(86) PCT No.: PCT/JP00/05502

§ 371 (c)(1),
(2), (4) Date: Apr. 1, 2002

(87) PCT Pub. No.: WO01/12807

PCT Pub. Date: Feb. 22, 2001

(30) Foreign Application Priority Data

Aug. 17, 1999 (JP) ................................. 11/230642

(51) Int. Cl.
*C12N 15/11* (2006.01)
(52) U.S. Cl. .................................................. 536/23.1
(58) Field of Classification Search ...................... None
See application file for complete search history.

(56) References Cited

OTHER PUBLICATIONS

Overbeek (1994, "Factors affecting transgenic animal production," Transgenic animal technology, pp. 96-98).*
Wall, 1996 Theriogenology, vol. 45, pp. 57-68.*
Houdebine, 1994, J. Biotech. vol. 34, pp. 269-287.*
Kappell, 1992, Current Opinions in Biotechnology, vol. 3, pp. 548-553.*
Cameron, 1997, Molec. Biol. 7, pp. 253-265.*
Mullins (1993, Hypertension, vol. 22, pp. 630-633).*
Mullins (1990, Nature, vol. 344, 541-544).*
Hammer (1990, Cell, vol. 63, 1099-1112).*
Mullins, 1989, EMBO J., vol. 8, pp. 4065-4072.*
Taurog, 1988, Jour. Immunol., vol. 141, pp. 4020-4023.*
Mullins (1996, J. Clin. Invest. vol. 98, pp. S37-S40).*
Niemann, 1997, Transg. Res. 7, pp. 73-75.*
Orkin and Motulsky (NIH ad hoc committee Dec. 1995—http:/www.nih.gov/news/panelrep.html).*
Theodore Friedmann (Scientific American Jun. 1997, pp. 96-101).*
Inder Verma et al (Nature Sep. 1997;389:239-242).*
Rubanyi GM (Molecular Aspects of Medicine (2001) 22:113-142).*
Human Gene Therapy 1996; 7:1781-1790.*
M. Aritomi et al., "Crystal Structure of Rat Bcl-$x_1$", J. Biol. Chem., vol. 272, No. 44, pp. 27886-27892, 1997.
W. Fang et al., "Cloning and Molecular Characterization of Mouse bcl-x in B and T Lymphocytes", J. Immunol., vol. 153, No. 10, pp. 4388-4394, 1994.
D.A.M. Grillot et al., "Genomic Organization, Promoter Region Analysis, and Chromosome Localization of the Mouse bcl-x Gene", J. Immunol., vol. 158, No. 10, pp. 4750-4757, 1994.
N. Shirakawa et al., "An Additional Form of Rat Bcl-x, Bcl-x β, Generated by an Unspliced RNA, Promotes Apoptosis in Promyeloid Cells", J. Biol. Chem., vol. 271, No. 22, pp. 13258-13265, 1996.
M. Gonzalez-Garcia et al., "bcl-x is the Major bcl-x mRNA form Expressed During Murine Development and its Product Localizes to Mitochondria", vol. 120, Development, No. 10, pp. 3033-3042, 1994.
J. L. Tilly et al., "Expression of Members of the Bcl-2 Gene Family in the Immature Rat Ovary: Equine Chorionic Gonatropin-Mediated Inhibition of Granulosa Cell Apoptosis is Associated with Decreased Bax and Constitutive Bcl-2 and Bcl-$x_{long}$ Messenger Ribonucleic Acid Levels", Endocrinology, vol. 136, No. 1, pp. 232-241, 1995.

* cited by examiner

*Primary Examiner*—Christopher H. Yaen
(74) *Attorney, Agent, or Firm*—Wenderoth, Lind & Ponack, L.L.P.

(57) ABSTRACT

The present invention provides an genetically engineered cDNA of the rat bcl-x gene, which has at least one substitution selected from the substitutions that change residues 22 Tyr to Phe, residues 26 Gln to Asn and residues 165 Arg to Lys, in the coding region of rat bcl-x cDNA of SEQ ID NO: 1, a recombinant vector containing the engineered cDNA, a cell into which the recombinant vector was introduced, and an improved protein of Bcl-$x_L$. The improved protein of Bcl-$x_L$ is useful as an ingredient for remedies for various diseases accompanied with cell death since it effectively inhibit cell death such as apoptosis.

20 Claims, 17 Drawing Sheets

A

B

C

SEQUENCE LISTING

```
<160> NUMBER OF SEQ ID NOS: 17

<210> SEQ ID NO 1
<211> LENGTH: 1742
<212> TYPE: DNA
<213> ORGANISM: Rattus norvegicus
<220> FEATURE:
<221> NAME/KEY: CDS
<222> LOCATION: (72)..(773)
<300> PUBLICATION INFORMATION:
<302> TITLE: An additional form of rat Bcl-x, Bcl-xbeta, generated
      by an unspliced RNA, promotes apoptosis in promyeloid
      cells.
<303> JOURNAL: J. Biol. Chem.
<304> VOLUME: 271
<305> ISSUE: 22
<306> PAGES: 13258-13265
<307> DATE: 1996-05-31

<400> SEQUENCE: 1
cacagagcag  acccagtgag  tgagcaggtg  ttttggacaa  tggactggtt  gagcccatct     60
ctattataaa a atg tct cag agc aac cgg gag ctg gtg gtt gac ttt ctc        110
            Met Ser Gln Ser Asn Arg Glu Leu Val Val Asp Phe Leu
              1               5                  10 tcc tac aag ctc tcc cag aaa gga tac agc tgg agt cag ttt agc gat        158
Ser Tyr Lys Leu Ser Gln Lys Gly Tyr Ser Trp Ser Gln Phe Ser Asp
         15                  20                  25 gtc gaa gag aac agg act gaa gcc cca gaa gaa act gaa cca gaa agg        206
Val Glu Glu Asn Arg Thr Glu Ala Pro Glu Glu Thr Glu Pro Glu Arg
 30                  35                  40                  45 gag acc ccc agt gcc atc aat ggc aac cca tcc tgg cac ctg gcg gat        254
Glu Thr Pro Ser Ala Ile Asn Gly Asn Pro Ser Trp His Leu Ala Asp
                 50                  55                  60 agc ccc gcg gtg aat gga gcc act ggc cac agc agc agt ttg gat gcg        302
```

```
                                                   -continued

Ser Pro Ala Val Asn Gly Ala Thr Gly His Ser Ser Leu Asp Ala
        65                  70                  75 cgg gag gta atc ccc atg gca gca gtg aag caa gcg ctg aga gag gct       350
Arg Glu Val Ile Pro Met Ala Ala Val Lys Gln Ala Leu Arg Glu Ala
            80                  85                  90 ggc gat gag ttt gaa ctg cgg tac cgg aga gca ttc agt gat cta aca       398
Gly Asp Glu Phe Glu Leu Arg Tyr Arg Arg Ala Phe Ser Asp Leu Thr
        95                  100                 105 tcc cag ctt cat ata acc cca ggg aca gca tat cag agc ttt gaa cag       446
Ser Gln Leu His Ile Thr Pro Gly Thr Ala Tyr Gln Ser Phe Glu Gln
110                 115                 120                 125 gta gtg aat gaa ctc ttt cgg gat ggg gta aac tgg ggt cgc att gtg       494
Val Val Asn Glu Leu Phe Arg Asp Gly Val Asn Trp Gly Arg Ile Val
                130                 135                 140 gcc ttc ttc tcc ttt ggc ggg gca ctg tgc gtg gaa agc gta gac aag       542
Ala Phe Phe Ser Phe Gly Gly Ala Leu Cys Val Glu Ser Val Asp Lys
                145                 150                 155 gag atg cag gta ttg gtg agt cgg att gca agt tgg atg gcc acc tac       590
Glu Met Gln Val Leu Val Ser Arg Ile Ala Ser Trp Met Ala Thr Tyr
            160                 165                 170 ctg aat gac cac cta gag cct tgg atc cag gag aac ggc ggc tgg gac       638
Leu Asn Asp His Leu Glu Pro Trp Ile Gln Glu Asn Gly Gly Trp Asp
        175                 180                 185 act ttt gtg gat ctc tac ggg aac aat gca gca gcc gag agc cgg aaa       686
Thr Phe Val Asp Leu Tyr Gly Asn Asn Ala Ala Ala Glu Ser Arg Lys
190                 195                 200                 205 ggc cag gag cgt ttc aac cgc tgg ttc ctg acg ggc atg act gtg gct       734
Gly Gln Glu Arg Phe Asn Arg Trp Phe Leu Thr Gly Met Thr Val Ala
                210                 215                 220 ggt gta gtt ctg ctg ggc tca ctc ttc agt cgg aag tga ccagacactg        783
Gly Val Val Leu Leu Gly Ser Leu Phe Ser Arg Lys
                225                 230 accgtccact cacctctcac ctcccacctt gccccacca caactctctc ttcagccacc       843
attgctacca ggagaaccac tacatgcaac tcacgcccct tcccctatta tagggttggg       903
cctagacgga gtcccctgca gttagctttc tagaatctac cacgcttctg tgaaagccac       963
cttcccccca catctcagtt cccttggcct caaaactcac aaggttttc ctcagatcag       1023
ctccttggag gctggcagga gtgggaaggg gtgtgctaga gggagaagag cctgccttgt       1083
tggtgggacc ctgattaccc ctgagcctct cgggaatgct tttctggcag ggagctggag       1143
agctctctaa acctcttccc ccagagacta gattgccttg gttttgatgt gtgtggcctc       1203
agaattgatc catttcccat tctgctgtgt ccctggggcg gctcctcctt cccatctcca       1263
cccccccccc cccagagcca ttgagtgagg tgcttttagc ccttttgact aactaaaaat       1323
gcaggctgct tgggataacg aggcaaggac ctcctcccca cctgtggcct ggccaagccc       1383
ccactcctgg tctgaatgtt ctcctgaggc tctggctag agtccagccc acccaggag         1443
gagggacgga gctgcggaaa gtccaccctg cgagagcctg agcggctctt gcggcttagc       1503
accaccccag atccttctcc accccctccc tggctccatg gtgaccatga ctgagggacc       1563
aactgggccc acgctaggtg ccccagagct gttaatgact tcagctgcct cacttcctgc       1623
aagatcagcc tgtggcatct ttgccttggg tgctggccac agggtccagg gactctggcc       1683
ttagcccaga agtgagagga agcttacagc gcagctatgg gagccctggg ggcttccct        1742

<210> SEQ ID NO 2
<211> LENGTH: 233
<212> TYPE: PRT
```

<213> ORGANISM: Rattus norvegicus

<400> SEQUENCE: 2

```
Met Ser Gln Ser Asn Arg Glu Leu Val Val Asp Phe Leu Ser Tyr Lys
 1               5                  10                  15
Leu Ser Gln Lys Gly Tyr Ser Trp Ser Gln Phe Ser Asp Val Glu Glu
                20                  25                  30
Asn Arg Thr Glu Ala Pro Glu Glu Thr Glu Pro Glu Arg Glu Thr Pro
            35                  40                  45
Ser Ala Ile Asn Gly Asn Pro Ser Trp His Leu Ala Asp Ser Pro Ala
        50                  55                  60
Val Asn Gly Ala Thr Gly His Ser Ser Ser Leu Asp Ala Arg Glu Val
 65                  70                  75                  80
Ile Pro Met Ala Ala Val Lys Gln Ala Leu Arg Glu Ala Gly Asp Glu
                85                  90                  95
Phe Glu Leu Arg Tyr Arg Arg Ala Phe Ser Asp Leu Thr Ser Gln Leu
            100                 105                 110
His Ile Thr Pro Gly Thr Ala Tyr Gln Ser Phe Glu Gln Val Val Asn
        115                 120                 125
Glu Leu Phe Arg Asp Gly Val Asn Trp Gly Arg Ile Val Ala Phe Phe
130                 135                 140
Ser Phe Gly Gly Ala Leu Cys Val Glu Ser Val Asp Lys Glu Met Gln
145                 150                 155                 160
Val Leu Val Ser Arg Ile Ala Ser Trp Met Ala Thr Tyr Leu Asn Asp
                165                 170                 175
His Leu Glu Pro Trp Ile Gln Glu Asn Gly Gly Trp Asp Thr Phe Val
            180                 185                 190
Asp Leu Tyr Gly Asn Asn Ala Ala Ala Glu Ser Arg Lys Gly Gln Glu
        195                 200                 205
Arg Phe Asn Arg Trp Phe Leu Thr Gly Met Thr Val Ala Gly Val Val
    210                 215                 220
Leu Leu Gly Ser Leu Phe Ser Arg Lys
225                 230
```

<210> SEQ ID NO 3
<211> LENGTH: 233
<212> TYPE: PRT
<213> ORGANISM: Artificial Sequence
<220> FEATURE:
<223> OTHER INFORMATION: Artificial Sequence: Modified Protein of SEQ ID NO: 2

<400> SEQUENCE: 3

```
Met Ser Gln Ser Asn Arg Glu Leu Val Val Asp Phe Leu Ser Tyr Lys
 1               5                  10                  15
Leu Ser Gln Lys Gly Phe Ser Trp Ser Asn Phe Ser Asp Val Glu Glu
                20                  25                  30
Asn Arg Thr Glu Ala Pro Glu Glu Thr Glu Pro Glu Arg Glu Thr Pro
            35                  40                  45
Ser Ala Ile Asn Gly Asn Pro Ser Trp His Leu Ala Asp Ser Pro Ala
        50                  55                  60
Val Asn Gly Ala Thr Gly His Ser Ser Ser Leu Asp Ala Arg Glu Val
 65                  70                  75                  80
Ile Pro Met Ala Ala Val Lys Gln Ala Leu Arg Glu Ala Gly Asp Glu
                85                  90                  95
Phe Glu Leu Arg Tyr Arg Arg Ala Phe Ser Asp Leu Thr Ser Gln Leu
```

-continued

```
                100                 105                 110
His Ile Thr Pro Gly Thr Ala Tyr Gln Ser Phe Glu Gln Val Val Asn
            115                 120                 125

Glu Leu Phe Arg Asp Gly Val Asn Trp Gly Arg Ile Val Ala Phe Phe
        130                 135                 140

Ser Phe Gly Gly Ala Leu Cys Val Glu Ser Val Asp Lys Glu Met Gln
145                 150                 155                 160

Val Leu Val Ser Lys Ile Ala Ser Trp Met Ala Thr Tyr Leu Asn Asp
                165                 170                 175

His Leu Glu Pro Trp Ile Gln Glu Asn Gly Gly Trp Asp Thr Phe Val
            180                 185                 190

Asp Leu Tyr Gly Asn Asn Ala Ala Glu Ser Arg Lys Gly Gln Glu
        195                 200                 205

Arg Phe Asn Arg Trp Phe Leu Thr Gly Met Thr Val Ala Gly Val Val
    210                 215                 220

Leu Leu Gly Ser Leu Phe Ser Arg Lys
225                 230
```

<210> SEQ ID NO 4
<211> LENGTH: 26
<212> TYPE: DNA
<213> ORGANISM: Artificial sequence
<220> FEATURE:
<223> OTHER INFORMATION: Artificial sequence: Synthesized
      oligonucleotide
<220> FEATURE:
<221> NAME/KEY: base
<222> LOCATION: (1)
<223> OTHER INFORMATION: n = a, c, t or g
<220> FEATURE:
<221> NAME/KEY: base
<222> LOCATION: (2)
<223> OTHER INFORMATION: n = a, c, t or g
<220> FEATURE:
<221> NAME/KEY: base
<222> LOCATION: (3)
<223> OTHER INFORMATION: n = a, c, t or g
<220> FEATURE:
<221> NAME/KEY: base
<222> LOCATION: (4)
<223> OTHER INFORMATION: n = a, c, t or g
<220> FEATURE:
<221> NAME/KEY: base
<222> LOCATION: (5)
<223> OTHER INFORMATION: n = a, c, t or g
<220> FEATURE:
<221> NAME/KEY: base
<222> LOCATION: (6)
<223> OTHER INFORMATION: n = a, c, t or g

<400> SEQUENCE: 4
nnnnnnacta gtggatcctg gaagag                                    26

<210> SEQ ID NO 5
<211> LENGTH: 28
<212> TYPE: DNA
<213> ORGANISM: Artificial sequence
<220> FEATURE:
<223> OTHER INFORMATION: Artificial sequence: Synthesized
      oligonucleotide

<400> SEQUENCE: 5
gcaatcttac tcaccaatac ctgcatct                                  28

<210> SEQ ID NO 6
<211> LENGTH: 27

```
<212> TYPE: DNA
<213> ORGANISM: Artificial sequence
<220> FEATURE:
<223> OTHER INFORMATION: Artificial sequence: Synthesized
      oligonucleotide

<400> SEQUENCE: 6
ggtgagtaag attgcaagtt ggatggc                                       27

<210> SEQ ID NO 7
<211> LENGTH: 19
<212> TYPE: DNA
<213> ORGANISM: Artificial sequence
<220> FEATURE:
<223> OTHER INFORMATION: Artificial sequence: Synthesized
      oligonucleotide

<400> SEQUENCE: 7
tcctggatcc aaggctcta                                                19

<210> SEQ ID NO 8
<211> LENGTH: 28
<212> TYPE: DNA
<213> ORGANISM: Artificial sequence
<220> FEATURE:
<223> OTHER INFORMATION: Artificial sequence: Synthesized
      oligonucleotide

<400> SEQUENCE: 8
gctaaagtta ctccagctgt atcctttc                                      28

<210> SEQ ID NO 9
<211> LENGTH: 31
<212> TYPE: DNA
<213> ORGANISM: Artificial sequence
<220> FEATURE:
<223> OTHER INFORMATION: Artificial sequence: Synthesized
      oligonucleotide

<400> SEQUENCE: 9
ctggagtaac tttagcgatg tcgaagagaa c                                  31

<210> SEQ ID NO 10
<211> LENGTH: 26
<212> TYPE: DNA
<213> ORGANISM: Artificial sequence
<220> FEATURE:
<223> OTHER INFORMATION: Artificial sequence: Synthesized
      oligonucleotide

<400> SEQUENCE: 10
ccagctgaat cctttctggg agagct                                        26

<210> SEQ ID NO 11
<211> LENGTH: 27
<212> TYPE: DNA
<213> ORGANISM: Artificial sequence
<220> FEATURE:
<223> OTHER INFORMATION: Artificial sequence: Synthesized
      oligonucleotide

<400> SEQUENCE: 11
aaaggattca gctggagtaa ctttagc                                       27

<210> SEQ ID NO 12
<211> LENGTH: 11
<212> TYPE: PRT
```

```
<213> ORGANISM: HIV-1

<400> SEQUENCE: 12

Tyr Gly Arg Lys Lys Arg Arg Gln Arg Arg
 1               5                   10

<210> SEQ ID NO 13
<211> LENGTH: 16
<212> TYPE: PRT
<213> ORGANISM: Drosophila

<400> SEQUENCE: 13

Arg Gln Ile Lys Ile Trp Phe Gln Asn Arg Arg Met Lys Trp Phe Lys
 1               5                   10                  15

<210> SEQ ID NO 14
<211> LENGTH: 30
<212> TYPE: DNA
<213> ORGANISM: Artificial sequence
<220> FEATURE:
<223> OTHER INFORMATION: Artificial sequence: Synthesized
      oligonucleotide

<400> SEQUENCE: 14
cgtcgtcgtg gtatgtctca gagcaaccgg                                    30

<210> SEQ ID NO 15
<211> LENGTH: 34
<212> TYPE: DNA
<213> ORGANISM: Artificial sequence
<220> FEATURE:
<223> OTHER INFORMATION: Artificial sequence: Synthesized
      oligonucleotide
<220> FEATURE:
<221> NAME/KEY: base
<222> LOCATION: (1)
<223> OTHER INFORMATION: n = a, c, t or g
<220> FEATURE:
<221> NAME/KEY: base
<222> LOCATION: (2)
<223> OTHER INFORMATION: n = a, c, t or g
<220> FEATURE:
<221> NAME/KEY: base
<222> LOCATION: (3)
<223> OTHER INFORMATION: n = a, c, t or g
<220> FEATURE:
<221> NAME/KEY: base
<222> LOCATION: (4)
<223> OTHER INFORMATION: n = a, c, t or g

<400> SEQUENCE: 15
nnnnaagctt catcacttcc gactgaagag tgag                               34

<210> SEQ ID NO 16
<211> LENGTH: 57
<212> TYPE: DNA
<213> ORGANISM: Artificial sequence
<220> FEATURE:
<223> OTHER INFORMATION: Artificial sequence: Synthesized
      oligonucleotide

<400> SEQUENCE: 16
catatgggtt atggtcgcaa aaaacgccgt cagcgtcgtc gtggtatgtc tcagagc      57

<210> SEQ ID NO 17
<211> LENGTH: 26
<212> TYPE: DNA
<213> ORGANISM: Artificial sequence
<220> FEATURE:
```

-continued

```
<223> OTHER INFORMATION: Artificial sequence: Synthesized
      oligonucleotide
<220> FEATURE:
<221> NAME/KEY: base
<222> LOCATION: (1)
<223> OTHER INFORMATION: n = a, c, t or g
<220> FEATURE:
<221> NAME/KEY: base
<222> LOCATION: (2)
<223> OTHER INFORMATION: n = a, c, t or g
<220> FEATURE:
<221> NAME/KEY: base
<222> LOCATION: (3)
<223> OTHER INFORMATION: n = a, c, t or g
<220> FEATURE:
<221> NAME/KEY: base
<222> LOCATION: (4)
<223> OTHER INFORMATION: n = a, c, t or g
<220> FEATURE:
<221> NAME/KEY: base
<222> LOCATION: (5)
<223> OTHER INFORMATION: n = a, c, t or g
<220> FEATURE:
<221> NAME/KEY: base
<222> LOCATION: (6)
<223> OTHER INFORMATION: n = a, c, t or g
<220> FEATURE:
<221> NAME/KEY: base
<222> LOCATION: (7)
<223> OTHER INFORMATION: n = a, c, t or g
<220> FEATURE:
<221> NAME/KEY: base
<222> LOCATION: (8)
<223> OTHER INFORMATION: n = a, c, t or g

<400> SEQUENCE: 17
nnnnnnnnca tatgggttat ggtcgc                                            26
```

MODIFIED CDNA OF RAT *BCL-X* GENE AND MODIFIED PROTEIN

This application is a 371 of PCT/JP00/05502 filed Aug. 17, 2000.

BACKGROUND OF THE INVENTION

1. Field of the Invention

The present invention relates to a genetically engineered cDNA of rat bcl-x gene and an improved protein. More particularly, it relates to a novel cDNA expressing an improved protein of Bcl-$x_L$ having higher apoptosis-inhibiting activity and cell death-inhibiting activity than the protein Bcl-$x_L$ expressed by the rat's apoptosis-inhibiting gene bcl-x. The invention also relates to materials for utilizing such cDNA in gene engineering, as well as to an improved protein of Bcl-$x_L$ expressed by the cDNA.

2. Description of the Related Art

Apoptosis is one of programmed cell death. Apoptosis is accompanied by poor contact with the surrounding cells, concentration of cytoplasm, condensation of the chromatin and nuclei associated with the endonuclease activity, fragmentation of the nuclei, formation of membrane-bounded apoptotic bodies, and phagocytosis of the apoptotic bodies by the adjacent macrophage or epithelial cells. A phenomenon that the chromosomal DNA is cleaved into DNA fragments of 180 to 200 base length by the endonuclease activity is also observed. Such phenomena have been discussed as the mechanism indicating that the apoptotic bodies are finally phagocytosed by the adjacent cells (for example, Immunology Today 7:115-119, 1986; Science 245:301-305, 1989).

As a gene controlling the apoptosis, for example, the gene bcl-2 which is an proto-oncogene found in the human follicular B cell lymphoma is known (Science 226 (4678): 1097-1099, 1984; Pro. Natl. Acad. Sci. USA 81(22): 7166-7170, 1984). Analysis of the gene structure and the transcripts or the cDNA clones have been also reported (Pro. Natl. Acad. Sci. USA 83(14): 5214-5218, 1986; Cell 47(1): 19-28, 1886). This bcl-2 gene is expressed in immune and nervous systems with high frequency. The gene product is considered to maintain homeostasis of the human immune and nervous systems by inhibiting apoptosis of the cells. Moreover, the bcl-2 gene is also considered to play an important role in morphogenesis during development since it is widely expressed particularly in the fetus Thereafter, homologues of the gene bcl-2 were found in bovine, rat, chicken, etc., and they are collectively called the bcl-2 family.

The inventors of the present application have cloned rat bcl-x gene as a homologue of the human bcl-x gene (Cell 74(4): 597-608, 1993) belonging to the bcl-2 family (J. Biol. Chem. 271(22): 13258-13265, 1996). They have also determined the three-dimensional structure of the Bcl-$x_L$ protein expressed from the rat bcl-x gene by X-ray analysis (J. Biol. Chem. 272(44): 27886-27892, 1997).

The inventors of the present application investigated the substitutions of amino acid residue causing conformational change to enhance the anti-apoptotic activity of rat Bcl-$x_L$. They genetically engineered cDNA of the bcl-x gene to replace a specific amino acid residue with other amino acid residue, and finally obtained the engineered cDNA whose product markedly inhibited cell death involving apoptosis. The invention of the present application was completed based on these new findings by the inventors. The purpose of the invention is to provide the engineered cDNA that allows expression of this novel improved protein of rat Bcl-$x_L$ in cells.

Another purpose of the invention is to provide a recombinant vector containing this engineered cDNA and a cell having the recombinant vector.

Still another purpose of the invention is to provide the improved protein expressed from the above-described engineered cDNA.

SUMMARY OF THE INVENTION

In order to solve the above-described problems, the present application provides the following inventions (1) to (8).

(1) A genetically engineered cDNA of the rat bcl-x gene, which has at least one substitution selected from the substitutions that change residues 22 Tyr to Phe, residues 26 Gln to Asn and residues 165 Arg to Lys, in the coding region of rat bcl-x cDNA of SEQ ID NO: 1.

(2) The genetically engineered cDNA of said invention (1), which is attached at its 5'-end with an oligonucleotide encoding a protein-transduction-domain peptide.

(3) The genetically engineered cDNA of said invention (2), wherein the oligonucleotide encodes the amino acid sequence of SEQ ID NO: 12 or 13.

(4) A recombinant vector carrying the genetically engineered cDNA of any one of said inventions (1) to (3).

(5) A cell into which the recombinant vector of said invention (4) is introduced.

(6) An improved protein produced from the genetically engineered cDNA of said invention (1), which has at least one amino acid substitution in SEQ ID NO: 2, which the amino acid substitution is selected from the substitutions of residues 22 Tyr with Phe, residues 26 Gln with Asn and residues 165 Arg with Lys.

(7). The improved protein of said invention (6), which is attached at the N-terminal with a protein-transduction-domain peptide.

(8). The improved protein of said invention (7), wherein the protein-transduction-domain peptide is an oligopeptide having the amino acid sequence of SEQ ID NO: 12 or 13.

DESCRIPTION OF THE PREFERRED EMBODIMENTS

Figure 1:
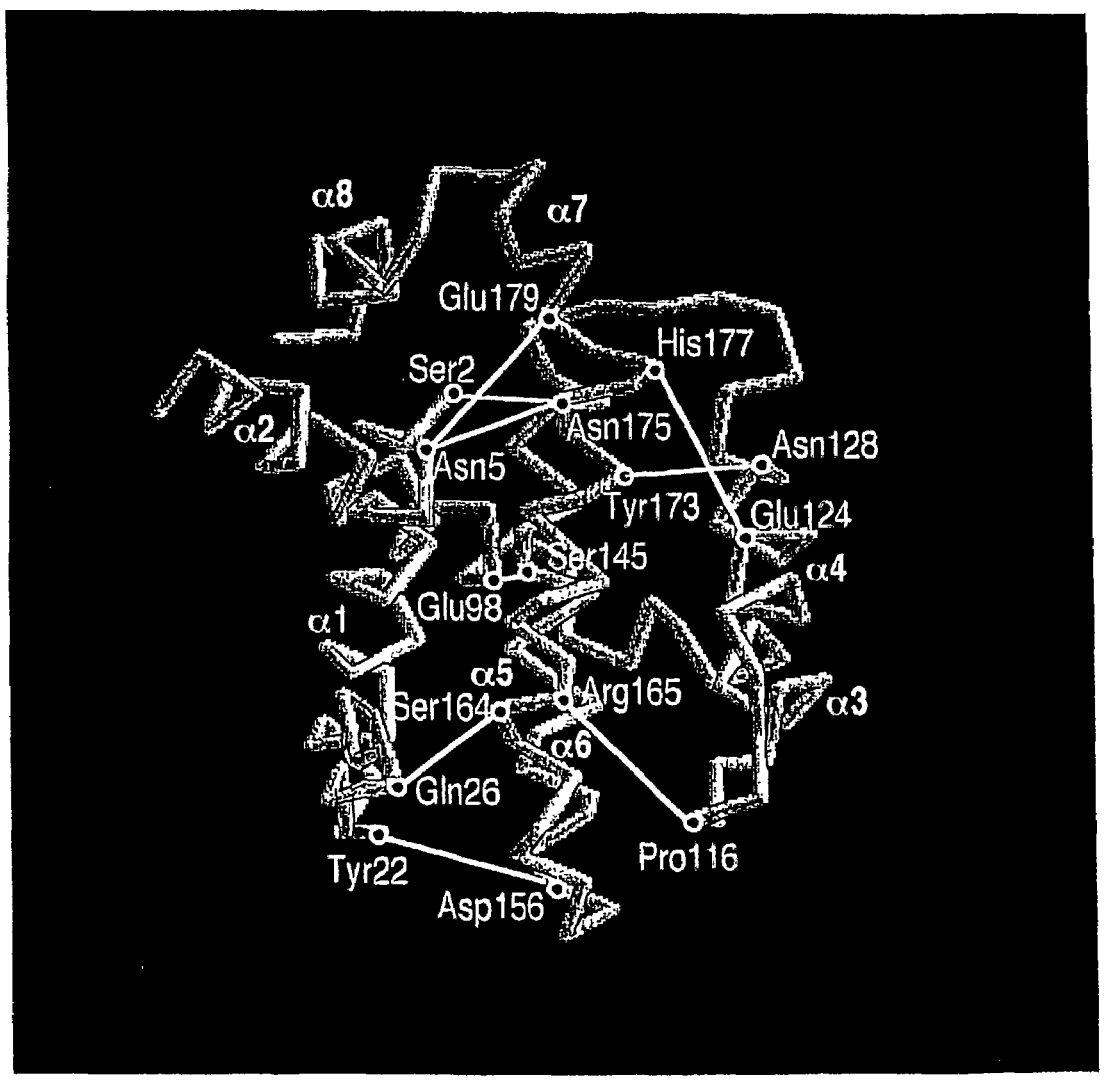
FIG. 1 shows the three-dimensional structure of the wild-type rat Bcl-$x_L$.

The engineered cDNA of the invention as indicated in the above invention (1), is characterized by having at least one substitution selected from the substitutions that change the codon of residues 22 Tyr (tac) to the codons of Phe (ttt/ttc), the codon of residues 26 Gln (cag) to the codons of Asn (aat/aac) and the codon of residues 165 Arg (cgg) to the codons of Lys (aaa/aag), in the coding region of rat bcl-x cDNA of SEQ ID NO: 1. In a preferred embodiment, the nucleotide substitutions have occurred in all the above 3 sites in the engineered cDNA of the invention (1). The engineered cDNA which has the nucleotide substitutions at the 3 sites produces the improved protein Bcl-xFNK as shown in the amino acid sequence of SEQ ID NO: 3. In this improved protein Bcl-xFNK, three hydrogen bonds between $Tyr^{22}$ and $Asp^{156}$, between $Gln^{26}$ and $Ser^{164}$ and between $Arg^{165}$ and $Pro^{116}$, which are formed in the wild-type rat Bcl-$x_L$ as shown in the three-dimensional structure of FIG. 1, are disturbed as a result of the amino acid substitutions (Tyr22Phe; Gln26Asn; Arg165Lys) caused by the above-described nucleotide substitutions.

The engineered cDNA may be prepared by a known method with a mutation kit or a PCR method as mentioned in Examples using the rat bcl-x cDNA as a template. For the cDNA of rat bcl-x, the plasmid pEF1-BOSbcl-x (J. Biol. Chem. 271(22): 13258-13265, 1996) can be used. An alternative method may be used, in which an oligonucleotide of any parts of the nucleotide sequence of SEQ ID NO: 1 is synthesized to use as a probe for screening of a rat cDNA library. Or an oligonucleotide that hybridizes with both ends of the cDNA fragment to be a subject may be synthesized and used as a primer in an RT-PCR method of preparing the cDNA from the mRNA isolated from rat cells.

The inventions (2) and (3) relates to a DNA fragment (polynucleotide) in which an oligonucleotide encoding a protein-transduction-domain peptide is ligated to the 5'-end of the engineered cDNA of the above invention (1). This DNA fragment can be used in preparation of the improved protein of Bcl-$x_L$ as mentioned below.

The recombinant vector in the invention (4) of the present application may be prepared by choosing an appropriate expression vector depending on a type of cell to be introduced (for example, prokaryotic cells such as *Escherichia coli* or *Bacillus subtilis*; eukaryotic cells such as yeast, insect cells, mammalian cells, or plant cells) and integrating therein the engineered cDNA of any one of the inventions (1) to (3). For example, when a microorganism such as *Escherichia coli* is employed, any of the engineered cDNAs of the above inventions (1) to (3) is integrated into the DNA cloning site of an expression vector having an replication origin functioning in a microorganism, promoter, ribosome-binding site, terminator, etc. When a eukaryotic cell such as a mammalian cell is employed, a recombinant vector of the invention (4) may be prepared using an expression vector for eukaryotic cells having a promoter, splice sites, a poly(A) site, etc.

The cell of the invention (5) is a cell into which the recombinant vector of the invention (4) is introduced and which produces the improved protein of Bcl-$x_L$. There is no limitation in the type of cell to be used. The recombinant vector of the invention (4) can be introduced into all of the cells, for example, prokaryotic cells such as *Escherichia coli* or *Bacillus subtilis*; eukaryotic cells such as yeast, insect cells, mammalian cells, or plant cells are included. Introduction of the recombinant vector into cells may be achieved by a known method. For example, when the recombinant vector is introduced into a mammalian cell, electroporation, a calcium phosphate method, a liposome method, a DEAE dextran method, and the like may be employed.

Among the cells of the invention (5), particularly, the mammalian cells can be also proliferated in a serum-free medium as shown in the data of the Examples below. In general, in order to keep a cultured cell alive for a certain period of time, it is necessary to add a serum (e.g., fetal bovine serum) containing growth factors to the culture medium. Addition of the growth factors can inhibit apoptosis of the cells to prolong the cellular life span. When cellular products such as physiologically active substances or monoclonal antibodies are recovered and purified from the culture medium in which mammalian cells are grown, however, it is desirous that the culture medium contains no impurities such as serum. The reason is that the cost increases and extra steps are required for purifying the objective substance, and that there is a possibility of the serum containing a risk factor such as a virus. The use of the serum-free and protein-free medium containing no serum, however, practically reduces the degree of cell growth and results in increasing dead cells, when the serum-free and protein-free media have been used. In addition, there is a problem that such increased dead cells might cause contamination of the cellular contents into the culture medium because of an outflow of the cellular contents from the dead cells.

On the other hand, there is an alternative method for proliferating cells without using any growth factor, wherein the cells are transfected with an proto-oncogene. In this method, however, it has been elucidated that apoptosis is rather promoted by expression of multiple proto-oncogene products.

The transfected mammalian cells of the invention (5) can be cultivated over a long period of time without accompanying apoptosis even in the absence of any growth factor such as serum since they express the improved protein of Bcl-$x_L$. Based on such excellent growth ability, it is possible to establish a cell line.

The improved protein of Bcl-$x_L$ of the invention (6) is expressed from the engineered cDNA of the invention (1). The protein is characterized by having at least one amino acid substitution in SEQ ID NO: 2, which substitution is selected from the substitutions of Tyr$^{22}$ with Phe, Gln$^{26}$ with Asn and Arg$^{165}$ with Lys. Bcl-xFNK that has the amino acid sequence of SEQ ID NO: 3 containing all of the amino acid substitutions as described above, is the most preferred embodiment.

In producing the improved proteins, the cells of the invention (5) are cultured to yield materials of culture, from which the improved proteins can be isolated and purified by combined known methods for isolation. The known methods for isolation include, for example, treatment with a denaturant or surface activator such as urea, ultra-sonication, digestion with an enzyme, salting-out or precipitation with a solvent, dialysis, centrifugation, ultra-filtration, gel filtration, SDS-PAGE, isoelectric focusing, ion exchange chromatography, hydrophobic chromatography, affinity chromatography, reverse phase chromatography, and the like.

The improved proteins can be used, for example, as active ingredients in apoptosis inhibitors or their leading compounds. Moreover, it is preferable to bind a protein-transduction-domain peptide to the N-terminal of the improved proteins of Bcl-$x_L$. The improved protein of Bcl-$x_L$ having the protein-transduction-domain peptide traverse the cell membrane and enter the cell to exhibit transiently a function of inhibiting apoptosis and cell death. Thus, the improved proteins acquiring such ability to traverse cell membranes can be utilized, for example in the following uses.

(a) To maintain cells to be used for implantation in a normal state over a long period of time.

(b) To maintain organs to be used for transplantation of organs in a normal state over a long period of time.

(c) To maintain organs subjected to hemostasis in a stable state during a surgical operation (d) To use as a therapeutic for cell death caused by cerebral ischemia accompanying cerebral thrombosis etc.

(e) To use as a therapeutic for fulminant hepatitis.

(f) To use as a preventive for cell death caused by excess administration of steroid hormones.

(g) To use as a therapeutic for diseases accompanied by muscular atrophy (e.g., muscular dystrophy, myasthenia, myopathy, etc.) caused by death of myocytes.

(h) To use as a preventive for the death of skin epithelial cells caused by injury or burn.

For a protein-transduction-domain peptides, an oligopeptide having the amino acid sequence as shown in SEQ ID NO: 12 or SEQ ID NO: 13 can be used. The oligopeptide of SEQ ID NO: 12 is PTD (protein transduction domain) of HIV-1 TAT. The oligopeptide of SEQ ID NO: 13 is PTD of a homeobox protein, Antennapedia, of *drosophila*.

With respect to these protein-transduction-domain peptides, for example, the amino acid sequence and cDNA sequence of HIV-1 TAT are known (Science, 285:1569-1572, 1999; GenBank Accession NO. U39362 M96155). The DNA fragment encoding the region (47th to 57th amino acid sequence of HIV TAT) corresponding to the PTD is ligated to the engineered cDNA of the invention (1) to give a fused DNA fragment (the invention (3)), which can be then expressed in a host cell such as *Escherichia coli* to produce the improved protein of Bcl-$x_L$ having the PTD peptide at the N-terminal. Antennapedia PTD is also known (e.g., GenBank Accession No. AE001573) and can be used to construct the PTD-fused improved protein in a similar manner. Alternatively, the improved protein of Bcl-$x_L$ is bound to a PTD peptide using a bivalent crosslinlking agent (e.g., EDC or β-alanine) to construct the improved protein of Bcl-$x_L$ bound to a protein-transduction-domain peptide.

EXAMPLES

The following examples serve to illustrate the invention specifically in more detail, but they are not intended to limit the scope of the invention.

Example 1

Preparation of Genetically Engineered cDNA

Two DNA fragments (bcl-xR165K, bcl-xY22F/Q26N) were generated by two-step PCR using as a template the cDNA clone of rat Bcl-$x_L$, pEF1-BOSbcl-x (J. Biol. Chem. 271:13258-13265, 1996). Finally, these DNA fragments were linked at the given regions to yield an engineered cDNA bcl-xFNK containing 3 amino acid substitutions (Tyr22Phe; Gln26Asn; Arg165Lys).

First, in order to construct bcl-xR165K containing the substitution of Arg165Lys, two DNA fragments (A and B) were synthesized by PCR. For the DNA fragment (A), the primer 1 shown in SEQ ID NO: 4 was used as the 5'-end primer, and the primer 2 shown in SEQ ID NO: 5 as the 3'-end primer. The primer 1 consists of the nucleotide sequence of the vector and the nucleotide sequence of the upstream of the coding region of bcl-x cDNA. It also contains the cleavage site of the restriction enzyme BamH I. The primer 2 is an antisense sequence of bcl-x cDNA, in which the codon of Arg$^{165}$ is substituted so as to code for Lys.

For the DNA fragment (B), the primer 3 shown in SEQ ID NO: 6 was used as the 5'-end primer, and the primer 4 shown in SEQ ID NO: 7 as the 3'-end primer. The primer 3 is a sense sequence of bcl-x cDNA, in which the codon of Arg$^{165}$ is substituted so as to code for Lys, and the nucleotide sequence of 5%-end half is complementary to that of 5'-end half of the primer 2. The primer 4 is an antisense sequence of bcl-x cDNA, which corresponds to the amino acid residues 178 to 184 of the coding region. It also contains the cleavage site of the restriction enzyme BamH I. PCR was carried out in the following conditions.

Reaction solution (volume 100 µl): 10 mM Tris-HCl, pH 8.3, 50 mM KCl, 1.5 mM $MgCl_2$, 0.001% gelatin, 0.2 mM each dATP, dCTP, dTTP, dGTP,
AmpliTaqGOLD: 2.5 U
A pair of primers: a combination of Primer 1 and Primer 2, and a combination of Primer 3 and Primer 4 (each primer: 1 µM)
Template DNA: 50 ng
Reaction condition 1: 94° C./10 min; (94° C./30 sec; 53° C./30 sec; 72° C./1 min)×15 cycles After the reaction, the two amplified DNA fragments (A and B) were purified by polyacrylamide gel electrophoresis. Then, the DNA fragments A and B (6 ng each) were added to the above-described PCR reaction solution (25 µl) to synthesize the respective complementary strands using AmpliTaqGOLD. The following reaction condition 2 was employed for the synthesis.

Reaction condition 2: 94° C./10 min; (94° C./30 sec; 41° C. to 47° C./30 sec; 72° C./1 min)×4 cycles After the reaction, a PCR reaction solution (75 µl) containing Primer 1, Primer 4 (final concentration: 1 µM each) and AmpliTaqGOLD (2.5 U) were added, and the PCR was carried out according to the above reaction condition 1. The 650-bp PCR product was purified by polyacrylamide gel electrophoresis and then treated with the restriction enzyme BamH I. On the other hand, pEF1-BOSbcl-x (having two BamH I sites) was treated with BamH I to yield two DNA fragments (5650 bp and 650 bp). The longer DNA fragment (5650 bp) was ligated to the above PCR product in a right orientation to yield the clone pEF1-BOSbcl-xR165K having an amino acid substitution of Arg165Lys.

To construct bcl-xY22F/Q26N, $Gln^{26}$ was first substituted with Asn, followed by the amino acid substitution of $Tyr^{22}$ with Phe. PCR was carried out using pEF1-BOSbcl-x (50 ng) as a template and a pair of the above Primer 1 and Primer 5 (SEQ ID NO:8). Another PCR was carried out using pEF1-BOSbcl-x (50 ng) as a template and a pair of the above Primer 4 and Primer 6 (SEQ ID NO:9). The components of the reaction solution (100 ml) were the same as above, and the reactions were performed according to the above-described condition 1. Primer 5 is the antisense sequence of bcl-xcDNA and contains the nucleotide substitutions to convert the codon of $Gln^{26}$ into a codon coding for Asn. Primer 6 is the sense sequence of bcl-x cDNA and contains the nucleotide substitutions to convert the codon of $Gln^{26}$ into a codon coding for Asn. The nucleotide sequence of 5'-end half of Primer 6 is complementary to that of 5'-end half of Primer 5. Two PCR products amplified by PCR were purified by polyacrylamide gel electrophoresis, and two DNA fragments (6 ng each) were mixed to synthesize the respective complementary strand using AmpliTaqGOLD. The condition for synthesis was the same as the above reaction condition 2. After the reaction, a PCR reaction solution (75 ml) containing Primer 1, Primer 4 (final concentration: 1 µM each) and AmpliTaqGOLD (2.5 U) were added, and the PCR was carried out according to the above reaction condition 1. The 650-bp PCR product was purified by polyacrylamide gel electrophoresis and then treated with the restriction enzyme BamH I. On the other hand, pEF1-BOSbcl-x was treated with BamH I to yield two DNA fragments (5650 bp and 650 bp). The longer DNA fragment (5650 bp) was ligated to the above PCR product in a right orientation to yield the clone pEF1-BOSbcl-xQ26N having an amino substitution of Gln26Asn.

Then, two PCR reactions were carried out independently using pEF1-BOSbcl-xQ26N as a template. One PCR contained a pair of the above Primer 1 and Primer 7 (SEQ ID NO: 10) and another PCR contained a pair of the above Primer 4 and Primer 8 (SEQ ID NO: 11). The components of the reaction solution (100 µl) were the same as above, and the reactions were performed according to the above-described condition 1. Primer 7 is the antisense sequence of bcl-x cDNA and contains the nucleotide substitution to convert the codon of $Tyr^{22}$ into the codon coding for Phe. Primer 8 is the sense sequence of bcl-x cDNA and contains the nucleotide substitution to convert the codon of $Tyr^{22}$ into the codon coding for Phe. The nucleotide sequence of 5'-end half of Primer 8 is complementary to that of 5'-end half of Primer 7. Two PCR products amplified by PCR were purified by polyacrylamide gel electrophoresis, and two DNA fragments (6 ng each) were mixed to synthesize the respective complementary strand using AmpliTaqGOLD. The condition for synthesis was the same as the above reaction condition 2. After the reaction, a PCR reaction solution (75 µl) containing Primer 1, Primer 4 (final concentration: 1 µM each) and AmpliTaqGOLD (2.5 U) were subjected to PCR according to the above reaction condition 1. The 650-bp PCR product was purified by polyacrylamide gel electrophoresis and then treated with the restriction enzyme BamH I. On the other hand, pEF1-BOSbcl-x was treated with BamH I to yield two DNA fragments (5650 bp and 650 bp). The longer DNA fragment (5650 bp) was ligated to the above PCR product in a right orientation to yield the clone pEF1-BOSbcl-xY22F/Q26N having two amino acid substitutions of Tyr22Phe and Gln26Asn.

Finally, pEF1-BOSbcl-xR165K and pEF1-BOSbcl-xY22F/Q26N were respectively cleaved with restriction enzymes (Bgl II and Kpn I). Then, the 1000-bp Bgl II/Kpn I DNA fragment having the amino acid substitutions of Tyr22Phe and Gln26Asn, derived from pEF1-BOSbcl-xY22F/Q26N, was ligated to the 5300-bp Bgl II/Kpn I DNA fragment having the amino acid substitution of Arg165Lys, derived from pEF1-BOSbcl-xR165K, to yield the engineered cDNA recombinant vector pEF1-BOSbcl-xY22F/Q26N/R165K coding for the improved protein Bcl-xFNK.

Example 2

Preparation of Transfected Cells

A murine premyeloid cell line FDC-P1 were cultured on RPMI1640 medium containing fetal bovine serum (10%) and a cytokine IL-3 (the supernatant of WEHI cell culture broth). A human leukemia cell line Jurkat were cultured on RPMI1640 medium containing fetal bovine serum (10%). The cells were incubated in a $CO_2$ incubator (5% $CO_2$/95% air, 37° C.).

The recombinant vector pEF1-BOSbcl-xY22F/Q26N/R165K prepared in Example 1 was amplified in *Escherichia coli* DH5αMCR (GIBCO BRL) and prepared using the Qiagen Plasmid midi Kit (Qiagen). The recombinant vector was cleaved with Sca I (one cleavage site) and the resulting linear DNA was dissolved in 1 mM EDTA solution.

The cells (FDC-P1 or Jurkat) were washed 3 times with an ice-cold K-PBS solution (30.8 mM NaCl, 120.7 mM KCl, 8.1 mM $Na_2HPO_4$, 1.46 mM $KH_2PO_4$) and suspended in K-PBS containing 5 mM $MgCl_2$ (Mg-K-PBS) at $10^7$ cells/ml. The cell suspension (0.4 ml) was mixed with Mg-K-PBS solution (0.4 ml) in an ice-cold cuvette (Electroporation Cuvettes Plus, 4-mm Gap, BTX, A Division of Genetronics). Then, the linearized pEF1-BOSbcl-xY22F/Q26N/R165K (10 μg) and the linearized DNA pST-neoB (0.5 μg) containing a drug geneticin-resistant gene were added thereto. Change of the volume by addition of the DNA was kept up to 1%. After 10-min incubation on ice, electroporation was carried out to introduce the recombinant vector into cells using the Gene Pulser (250 μF and 330V, BioRad). After 10-min incubation on ice, the cells were gently suspended in 39 ml of the fresh culture medium in a 100-mm dish and incubated in a $CO_2$ incubator. After a lapse of 1 day, the cells were divided and placed in a 96-well plate. Geneticin (GIBCO BRL) was added at 200 μg/ml for FDC-P1 cells and at 1 mg/ml for Jurkat cells to select the geneticin-resistant cells.

Example 3

Analysis of Expression Level of the Improved Bcl-xFNK

The expression level of the improved protein Bcl-xFNK in the transfected cells prepared in Example 2 was examined by Western blotting. The cells were washed once with PBS (pH 7.4; NaCl 137 mM, $Na_2HPO_4$ 8.1 mM, KCl 2.68 mM, $KH_2PO_4$ 1.47 mM). After addition of 2% SDS (sodium dodecylsulfate) solution, the cells were disrupted by sonication to solubilize the whole proteins. The proteins were quantitatively analyzed by the BCA Protein Assay (PIERCE), and 20 μg of protein was fractionated on SDS-polyacrylamide gel electrophoresis (Lemli's system). After the electrophoresis, the protein was blotted on a PVDF membrane (Amersham Pharmacia Biotec). The membrane was immersed in a blocking solution containing fetal bovine serum (10%), and then immersed in a TBS solution (Tris-HCl pH 7.4 20 mM, NaCl 136 mM, Tween 80 0.2%) containing the murine monoclonal antibody 105-1 (0.5 μg/ml) that reacts with the C-terminal of rat $Bcl-x_L$. After incubation at 37° C. for 1 hour, the membrane was washed well with TBS, then immersed in a TBS solution containing an HRP (horse radish peroxidase)-binding or AP (alkaline phosphatase)-conjugated secondary antibody, and incubated at 37° C. for 1 hour. The HRP-conjugated secondary antibodies binding to $Bcl-x_L$ and Bcl-xFNK were visualized on an X-ray film using the RENAISSANCE kit (NEN Life Science Product). The AP-conjugated antibodies binding to $Bcl-x_L$ and Bcl-xFNK were visualized with the fluoro-image analyzer FLA-2000 (Fuji film) using the ATTOPHOS kit (Boehringer).

Figure 2:
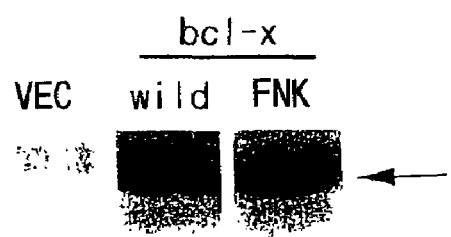
FIG. 2 shows the results of Western blotting analysis of the expression level of the improved protein Bcl-xLFNK in the transfected cell.

The results are shown in FIG. 2. It was confirmed that the cell transfected with the recombinant vector pEF1-BOSbcl-xFNK expresses a protein having the same molecular weight (about 30 kDa) as that expressed in the cells transfected with the clone pEF1-BOSbcl-x of the wild-type $Bcl-x_L$.

Example 4

Confirmation of Resistance to the Death of the Jurkatbcl-xFNK Transfectant

For the transfected Jurkatbcl-xFNK cells prepared in Example 2, the resistance (non-sensitivity) to a variety of apoptosis-inducing stimuli was examined. The results are shown in FIGS. 3 to 13. In these figures, the empty circle (○) represents the transfectant Jurkatbcl-xFNK expressing the improved Bcl-xFNK. The filled circle (●) represents the transfectant Jurkatbcl-x expressing the wild-type $Bcl-x_L$ at the same expression level. The empty square (□) represents Jurkatvec cell transfected with the empty vector plasmid DNA. The empty diamond (◇) represents the parent cell Jurkat used in the transfection experiments.

(a) Resistance to Apoptosis Induced by Serum Withdrawal

The cells were washed 3 times with PBS and suspended in RPMI1640 medium containing no serum at $1 \times 10^5$ cells/ml. The cells were incubated in a $CO_2$ incubator and the surviving cells were counted by the trypan blue exclusion everyday. The number of the cells was carefully controlled to be less than $5 \times 10^5$ cells/ml. When the cell number was expected to exceed the limitation, the culture medium was diluted 2 fold. Every 3 days, the half of the serum-free medium was replaced with the fresh medium.

Figure 3:
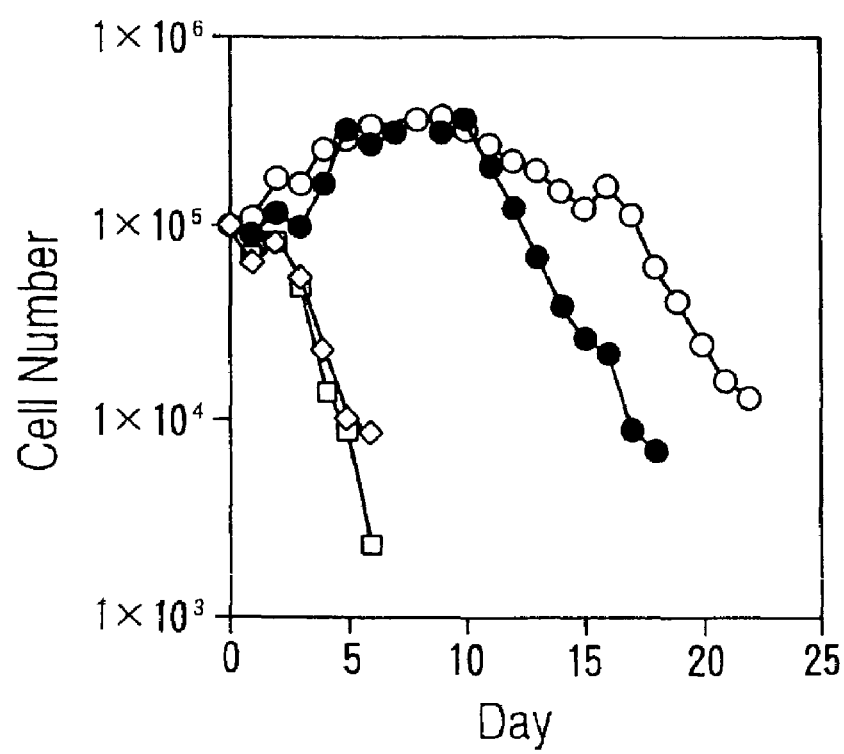
FIG. 3 shows the results of a test for resistance of the transfected cells to apoptosis induced by serum depletion.

As shown in FIG. 3, the transfected cells expressing the wild-type $Bcl-x_L$ was resistant to the serum withdrawal and survived longer than the control parent cells and the vector-transfected cells. The transfected cells expressing the improved Bcl-xFNK survived for a longer period than the wild-type $Bcl-x_L$-expressing cells, from which an excellent apoptosis inhibition effect of Bcl-xFNK was confirmed. Moreover, it was confirmed that the transfected cells could be cultured on serum-free medium.

(b) Resistance to Anti-Fas Antibody

The cells were suspended in RPMI1640 medium at $1 \times 10^5$ cells/ml, to which anti-Fas antibody (clone CH-11; MBL) was then added at a concentration of 1, 10, 100, or 1000 ng/ml. After incubation for 1 day, the surviving cells were counted by the trypan blue exclusion.

Figure 4:
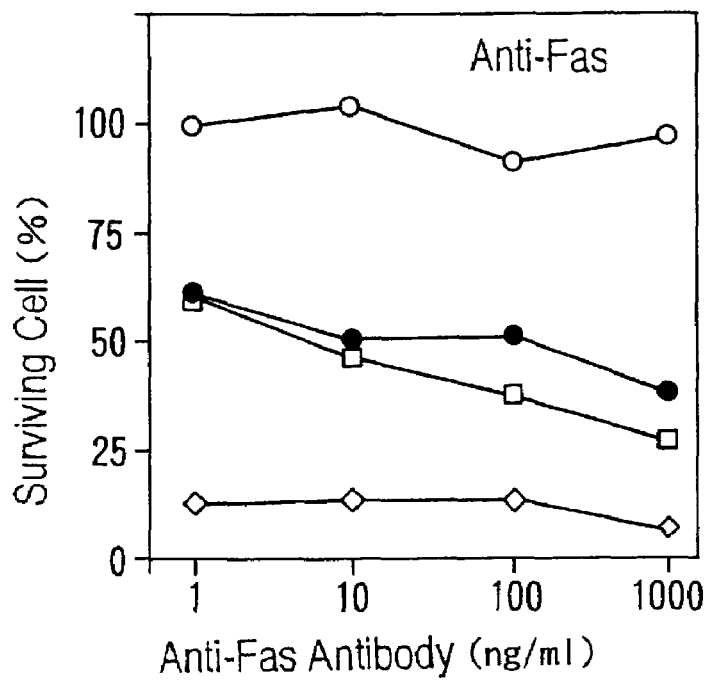
FIG. 4 shows the results of a test for resistance of the transfected cells to anti-Fas antibody.
Figure 5:
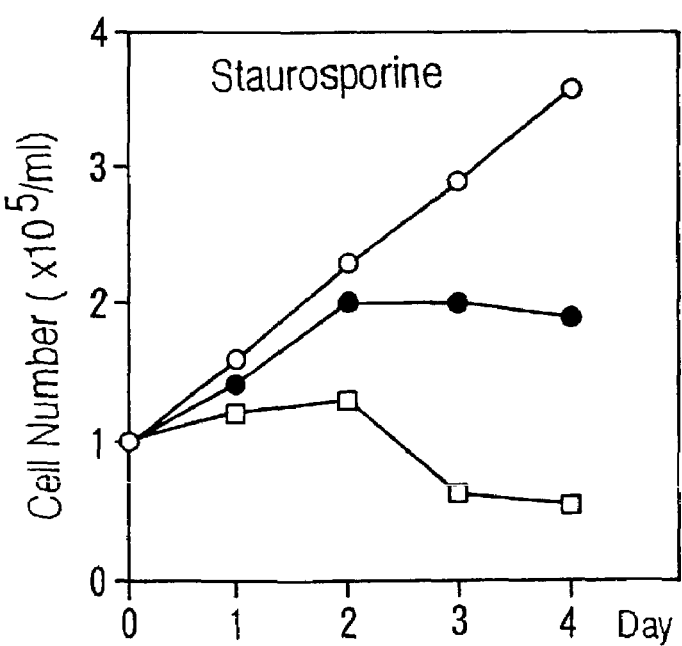
FIG. 5 shows the results of a test for resistance of the transfected cells to staurosporine.
Figure 6:
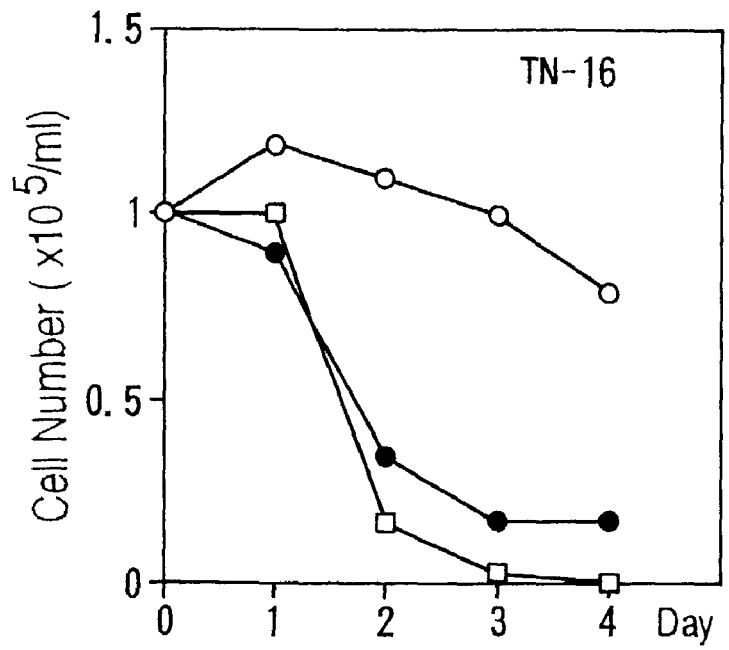
FIG. 6 shows the results of a test for resistance of the transfected cells to TN-16.
Figure 7:
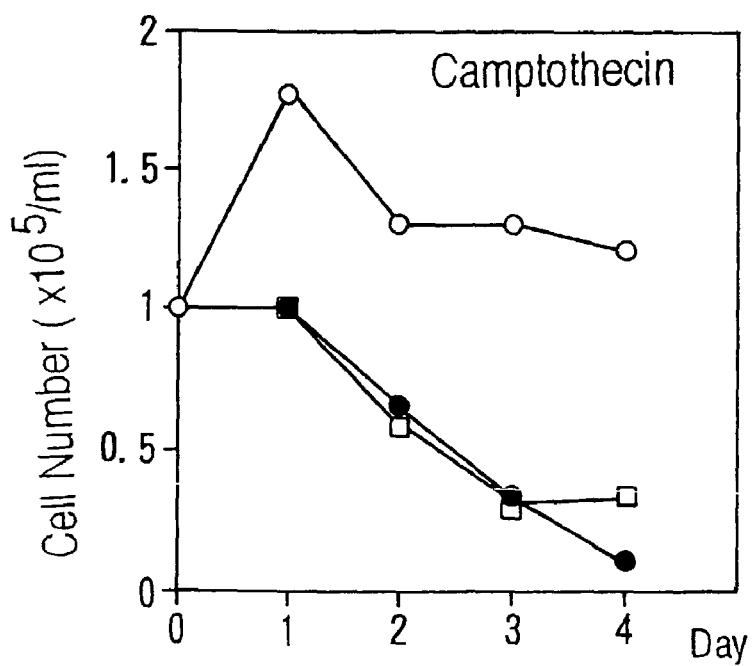
FIG. 7 shows the results of a test for resistance of the transfected cells to camptothecin.
Figure 8:
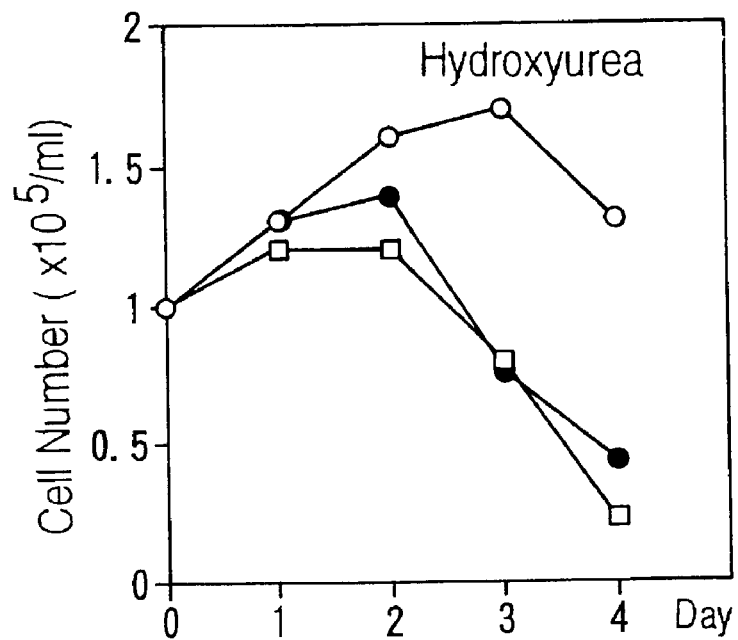
FIG. 8 shows the results of a test for resistance of the transfected cells to hydroxyurea.
Figure 9:
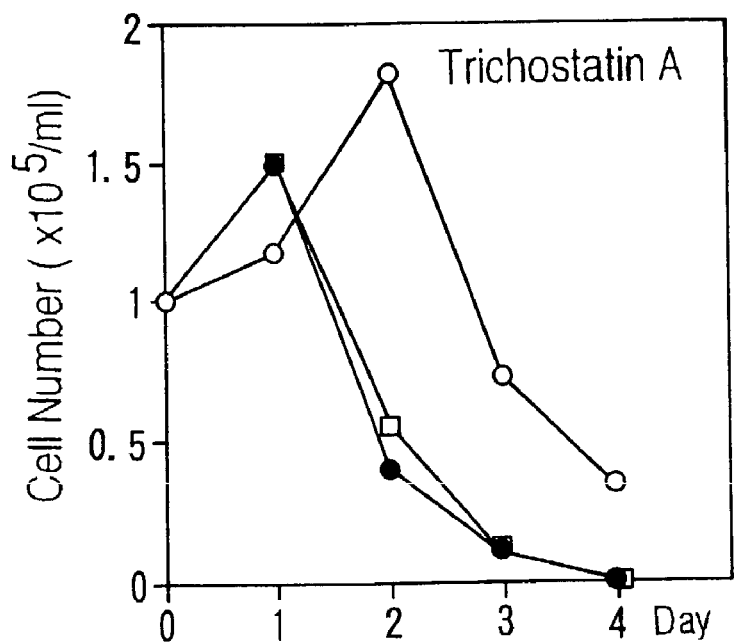
FIG. 9 shows the results of a test for resistance of the transfected cells to trichostatin A.
Figure 10:
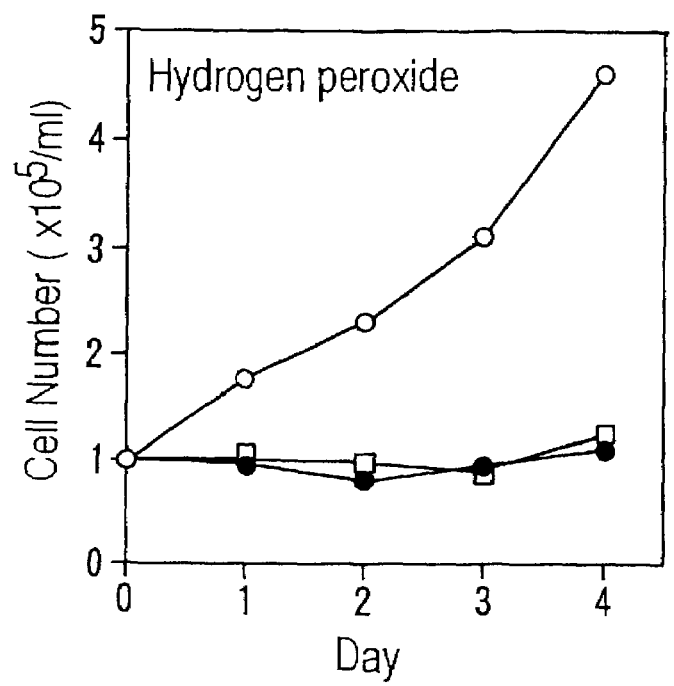
FIG. 10 shows the results of a test for resistance of the transfected cells to hydrogen peroxide.
Figure 11:
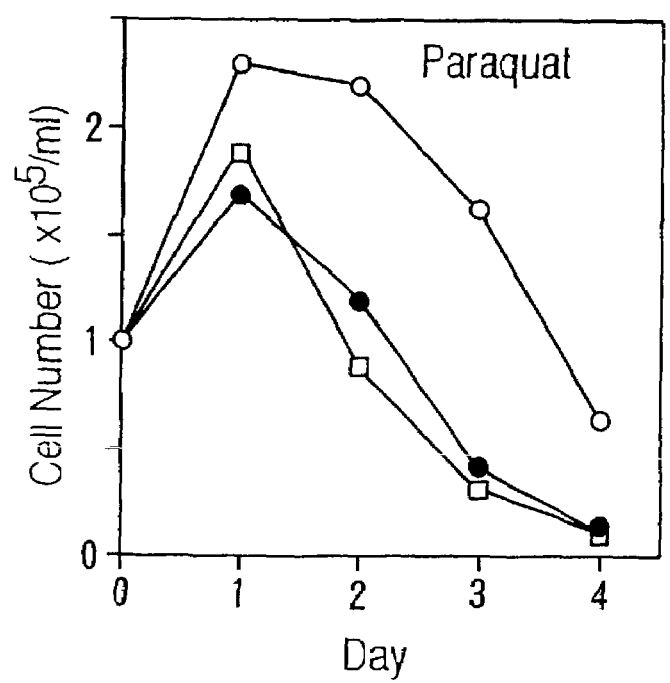
FIG. 11 shows the results of a test for resistance of the transfected cells to paraquat.
Figure 12:
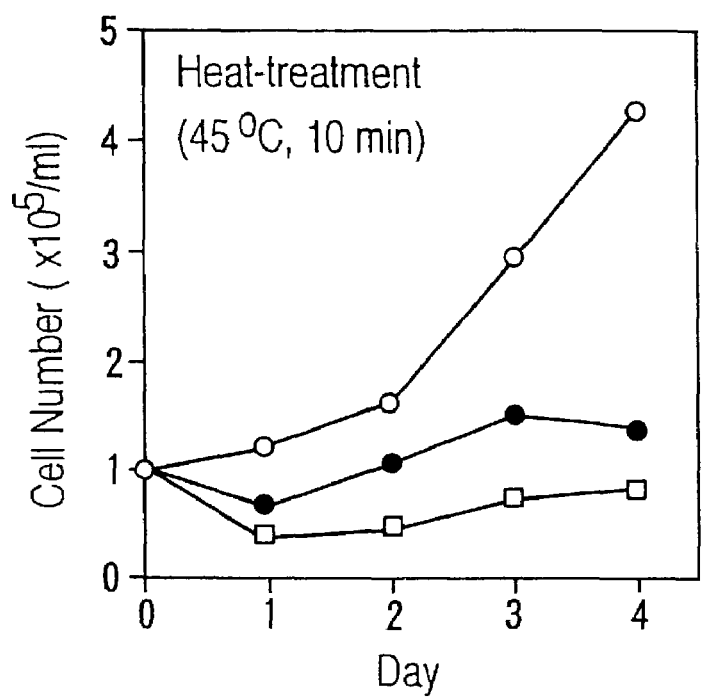
FIG. 12 shows the results of a test for resistance of the transfected cells to heat treatment.

The results are shown in FIG. 4, wherein the number of the cells incubated without the antibody was taken as 100%. As seen clearly from FIG. 4, the transfectant expressing the improved Bcl-xFNK exhibited high resistance to the highly concentrated anti-Fas antibody.

(c) Resistance to a Variety of Cytotoxic Drugs Including Anti-Cancer Agents

The cells were suspended in RPMI1640 medium at $1 \times 10^5$ cells/ml, to which staurosporine (20 nM), TN-16 (10 μM), camptothecin (10 μM), hydroxyurea (1 mM), trichostatin A (0.25 μg/ml), hydrogen peroxide (0.05 mM), or paraquat (1 mM) was then added. And the cells were incubated. The surviving cells were counted by the trypan blue exclusion everyday.

As seen from the results shown in FIGS. 5 to 11, the transfectant expressing the improved Bcl-xFNK exhibited high resistance to all of the cytotoxic drugs tested.

(d) Resistance to Heat Treatment

Figure 13:
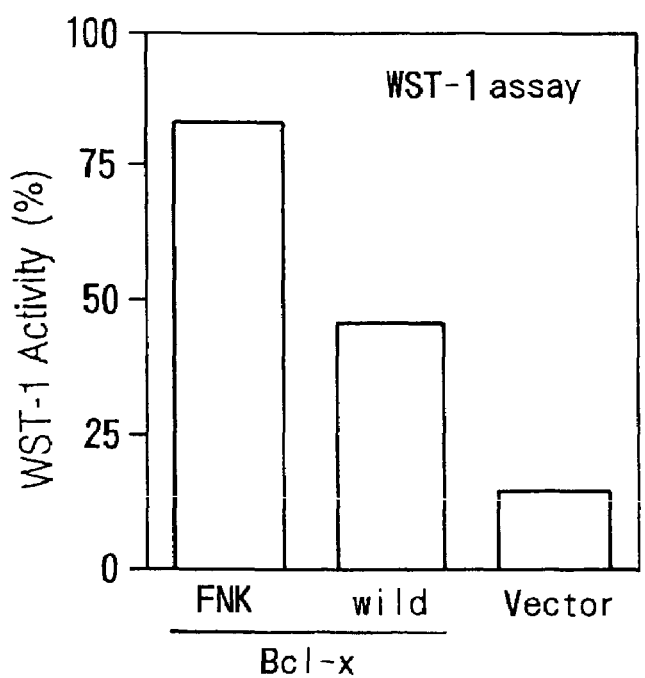
FIG. 13 shows the results of a test for dehydrogenase activity in the transfected cells after heat treatment by the WST-1 assay.

The cells were suspended in RPMI1640 medium at $1 \times 10^5$ cells/ml, and incubated at 45° C. for 10 minutes. The cells were harvest by centrifugation, then suspended in an equal amount of the fresh culture medium, and incubated at 37° C. The surviving cells were counted by the trypan blue exclusion everyday and shown in FIG. 12. In addition, dehydrogenase activities of the cells (100 μl of the culture broth) were determined at 1st day using the Cell Counting Kit (Dojin Chemical) and WST-1 as a substrate (WST-1 Assay). The results are shown in FIG. 13, wherein the enzyme activity of the cells without heat treatment was taken as 100%.

As seen from the above results, it was confirmed that the transfectant expressing the improved Bcl-xFNK exhibited high resistance to heat treatment, and the dehydrogense activity was maintained at high level even after heat treatment.

Example 5

Figure 14:
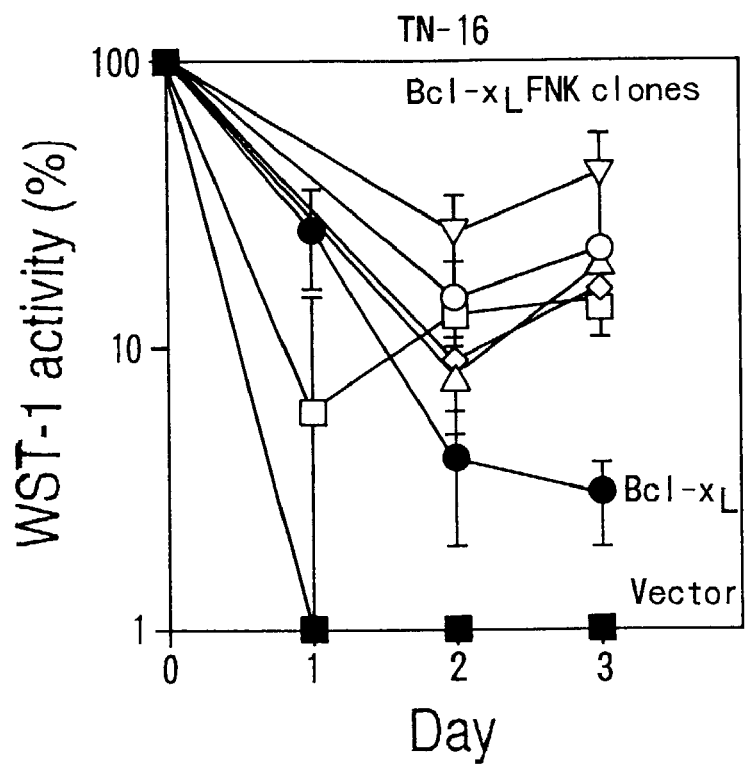
FIG. 14 shows the results of a test for dehydrogenase activity in the transfected cells treated with TN-16 by the WST-1 assay.
Figure 15:
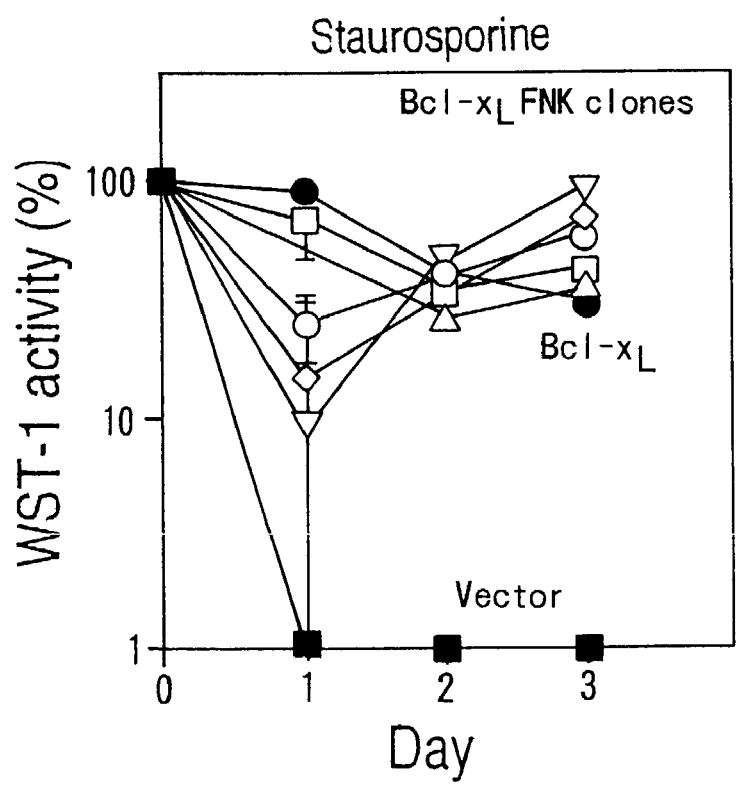
FIG. 15 shows the results of a test for dehydrogenase activity in the transfected cells treated with staurosporine by the WST-1 assay.
Figure 16:
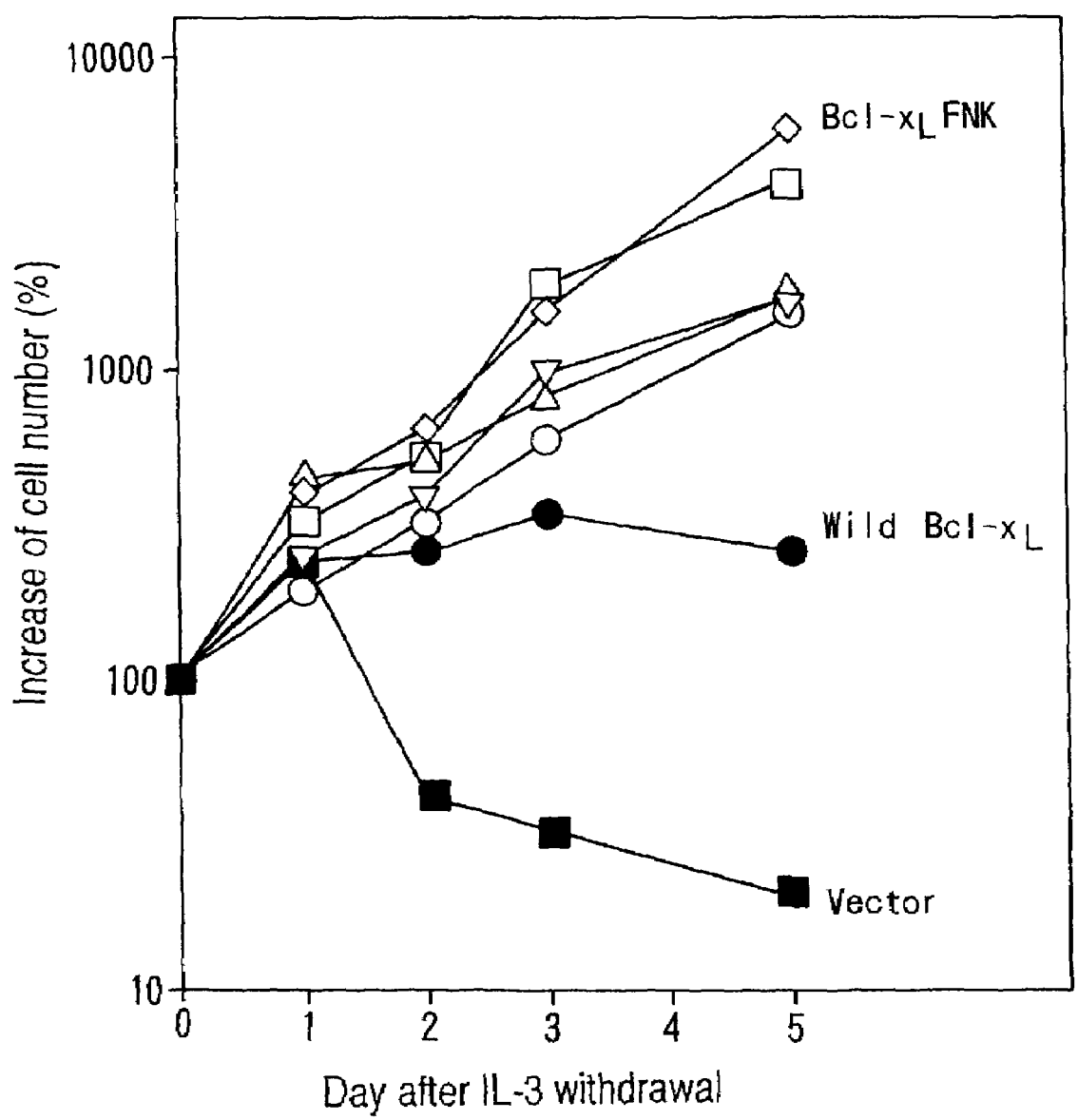
FIG. 16 shows the results of a test for resistance of the transfected cells to apoptosis induced by depletion of the cytokine IL-3.

Confirmation of the Resistance to the Cell Death of the FDC-P1bcl-xFNK Transfectants For the transfectant FDC-P1bcl-xFNK cells prepared in Example 2, the resistance was examined to a variety of apoptosis-inducing stimuli. The results are shown in FIGS. 14 to 16. In these figures, the empty marks, ◇, □, △, ▽, and ○ represent 5 independent transfectants, FDC-P1bcl-xFNK-1, -2, -3, -4, and -5, respectively. The mark ● represents the transfectant FDC-P1bcl-x expressing the wild-type Bcl-$x_L$ at the same expression level. The mark ■ represents FDC-P1vec in which the empty vector plasmid DNA has been introduced.

(a) Resistance to TN-16 and Staurosporine

The cells were suspended in culture medium at $2\times10^5$ cells/ml, to which TN-16 (50 µM) and staurosporine (10 nM) was then added. The dehydrogenase activity of the cells (100 µl of the culture broth) was determined daily using the Cell Counting Kit (Dojin Chemical) and WST-1 as a substrate (WST-1 Assay). The enzyme activity was taken as 100% immediately before addition of the agents.

The results are shown in FIGS. 14 and 15. It was confirmed that all independent transfectants expressing the improved Bcl-xFNK exhibited high resistance to treatment with TN-16 and staurosporine, and the dehydrogenase activity was maintained at high level.

(b) Resistance to Apoptosis Induced by Depletion of the Cytokine IL-3

The cells were washed 3 times with PBS and suspended in culture medium containing no IL-3 (but containing serum) at about $5\times10^4$ cells/ml, and the surviving cells were counted by the trypan blue exclusion everyday. The result are shown in FIG. 16, in which the number of the surviving cells immediately after depletion of IL-3 was taken as 100%. In this experiment, the cells other than FDC-P1vec were diluted 5 times with the fresh medium containing no IL-3 every 3rd day.

As seen clearly from FIG. 16, it was confirmed that the transfectants expressing the improved Bcl-xFNK exhibited higher resistance than the transfectant expressing the wild-type Bcl-$x_L$ to apoptosis induced by depletion of IL-3, and that they could grow even in the absence of IL-3.

Example 6

Preparation of CHO Transfectants

Chinese hamster ovary cell CHO were transfected with the recombinant vector pEF1-BOSbcl-xY22F/Q26N/R165K prepared in Example 1.

The CHO cells ($1\times10^5$ cells) were suspended in culture medium DMEM/F-12 (GIBCO BRL) containing 10% fetal bovine serum, and incubated in a 60-mm dish overnight. The linearized pEF1-BOSbcl-xY22F/Q26N/R165K (10 µg) and the linearized pST-neoB (0.5 µg) having a drug Geneticin-resistant gene were introduced into the CHO cells using a SuperFect Transfection Reagent kit (Qiagen). As a control, the linearized empty vector pEF1-BOS or the linearized pEF1-BOSbcl-x were introduced together with the linearized pST-neoB into the CHO cells. After the transfection treatment, the cells were incubated in culture medium DMEM/F-12 containing 10% fetal bovine serum overnight. Geneticin (700 µg/ml) was added, and the incubation was continued to yield the transfected cells. In the same manner as in Example 3, the transfectants expressing the improved protein Bcl-xFNK or the wild-type Bcl-$x_L$ abundantly and to the same level were selected. Thus, CHObcl-x, CHObcl-xFNK, and CHOvec (transfected with the empty vector) were obtained.

Example 7

Incubation of the CHO Transfectants in Serum-Free Medium

Three transfectants, CHObcl-x, CHObcl-xFNK, and CHOvec, prepared in Example 6 were incubated in culture medium DMEM/F-12 containing 10% fetal bovine serum. The cells ($1\times10^3$ cells) were plated in a 100-mm dish containing the medium DMEM/F-12 containing 3% fetal bovine serum. For 5 consecutive days, two thirds of the culture medium was replaced with the DMEM/F-12 containing no fetal bovine serum. The cells were incubated on the medium lacking serum from day 6. The incubation was further continued for another 6 days.

Figure 17:
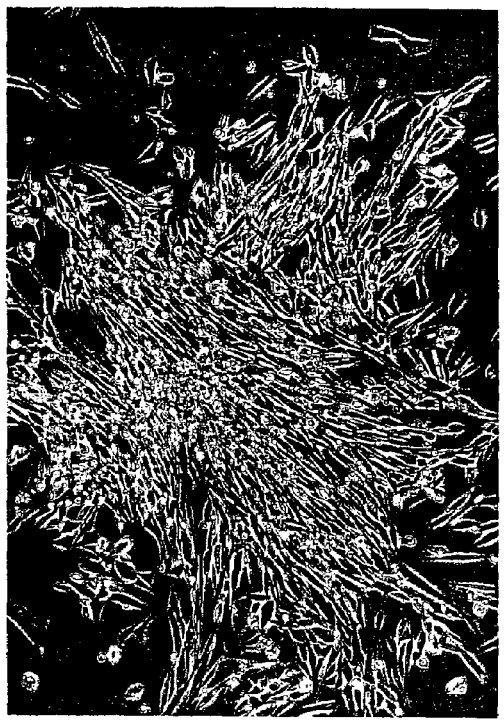
FIG. 17 is a microscopic photograph showing the transfected CHO cells growing in a serum-free medium.
Figure 17:
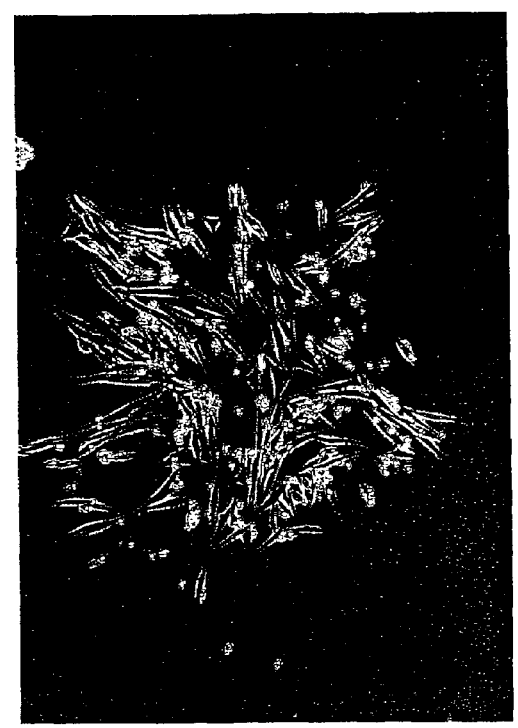
Figure 17:
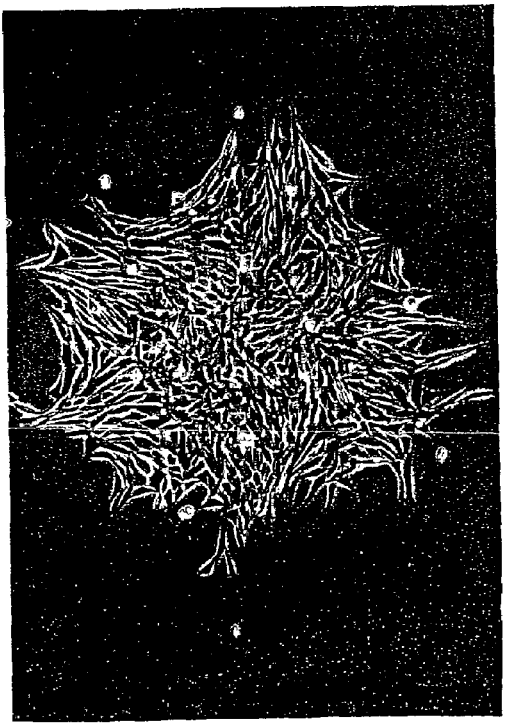

The results are shown in the photograph of FIG. 17. CHObcl-xFNK expressing the improved Bcl-xFNK (FIG. 17C) grew far better than CHOvec (FIG. 17B) to which the empty vector was introduced. Additionally, fewer cells were dying or dead and the cells more firmly contacted each other without space in CHObcl-xFNK colonies than those in the colonies of CHObcl-x cells expressing Bcl-$x_L$ (FIG. 17A).

From the above results, it was confirmed that the transfected cells of the invention could grow well in a normal state even in a serum-free medium.

Example 8

Construction of a Recombinant Vector Expressing the TAT-Bcl-xFNK Protein

The engineered cDNA coding for Bcl-xFNK prepared in Example 1 was fused to the cDNA coding for the protein transduction domain of TAT protein of HIV virus by 2-step PCR. PCR was carried out using Primer 9 (SEQ ID NO: 14) as the 5'-end primer, Primer 10 (SEQ ID NO: 15) as the 3'-end primer and the recombinant vector pEF1-BOSbcl-xY22F/Q26N/R165K having Bcl-xFNK cDNA as a template. Primer 9 is the sense sequence consisting of the 3'-end of TAT-PTD cDNA and the 5'-end (containing the initiation codon) of Bcl-xFNK cDNA. Primer 10 is the antisense sequence consisting of the 3'-end (containing a termination codon) of Bcl-xFNK cDNA and the cleavage site for the restriction enzyme Hind III. Details of the PCR reaction are as follows Reaction solution (volume 100 µl): 10 mM Tris-HCl, pH 8.3, 50 mM KCl, 1.5 mM $MgCl_2$, 0.001% gelatin, 0.2 mM each dATP, dCTP, dTTP, dGTP, AmpliTaqGOLD: 2.5 U Primers: a combination of Primer 9 and Primer 10 (each primer: 1 µM)

Template DNA: 50 ng

Reaction condition 3: 94° C./10 min (94° C./30 sec; 49° C./30 sec; 72° C./1 min)×15 cycles.

After the reaction, the amplified DNA fragment was purified by polyacrylamide gel electrophoresis. To the above-described PCR reaction solution (25 µl) was added the purified DNA fragment (25 ng) and Primer 11 (SEQ ID NO: 16) to synthesize the complementary strand using AmpliTaqGOLD. Primer 16 is the 5'-end sense sequence coding for the amino add sequence of TAT-PTD flanked by Met (initiation codon)-Gly at the 5'-end and Gly- the initiation codon of Bcl-xFNK cDNA at the 3'-end, as shown in SEQ ID NO: 12. The condition for synthesis is as follows.

Reaction condition 4: 94° C./10 min (94° C./30 sec; 53° C. to 59° C./30 sec; 72° C./1 min)×5 cycles After the reaction, the PCR solution (75 μl) containing Primer 12 (SEQ ID NO: 17), Primer 10 (final concentration: 1 μM each), and AmpliTaqGOLD (2.5 U) was added, and the PCR was carried out according to the above reaction condition 3. Primer 12 is a sense sequence coding for Met-Gly and the subsequent N-terminal three amino acid residues of TAT-PTD with a cleavage site of the restriction enzyme Nde I at the 5'-end. The amplified DNA fragment was purified by polyacrylamide gel electrophoresis. After cleavage with Nde I, the cleaved end was made blunt with T4DNA polymerase and further subjected to be digested with Hind III. The *Escherichia coli* expression vector pROEX1 (Life Technologies) was cleaved with Nco I, then made blunt with nuclease S1, followed by digestion with Hind III. Two DNAs were ligated to each other to yield the recombinant vector pROEX1-bcl-xY22F/Q26N/R165K coding for TAT-Bcl-xFNK in which a protein-transduction-domain peptide of TAT protein is fused at the N-terminal.

Example 9

Preparation of TAT-Bcl-xFNK Protein

TAT-Bcl-xFNK protein was expressed in *Escherichia coli* and partially purified as described below. *Escherichia coli* DH5αMCR carrying pROEX1-bcl-xY22F/Q26N/R165K was incubated on 1000 ml of LB liquid medium (5 g yeast extract, 10 g Bactotrypton, and 5 g NaCl) containing ampicillin (50 μg/mg) with shaking at 37° C. When the cells reached at the logarithmic growth phase (O.D.600=0.5), IPTG (isopropyl-1-thio-β-galactoside; final concentration 1 mM) was added, and the incubation was continued for 2 hours. TAT-Bcl-xFNK protein was prepared from a soluble fraction and an insoluble fraction (inclusion body) after disrupting the cells. The protein was prepared from the soluble fraction as follows. The harvested cells were washed 3 times with PBS, then suspended in 40 ml of Buffer A (50 mM Tris-HCl pH 8.0, 150 mM NaCl, 1 mM EDTA, 1 mM PMSF), and disrupted by ultrasonication. After centrifugation, TAT-Bcl-xFNK was purified from the supernatant by antibody-affinity chromatography using a column in which was packed a monoclonal antibody 35-32 bound to carriers, said monoclonal antibody being derived from a mouse and recognizing the N-terminal region of rat Bcl-$x_L$. TAT-Bcl-xFNK was bound to the antibody, washed, and then eluted with an eluate (50 mM Glycine-HCl pH 2.7, 50 mM NaCl). The eluate was neutralized with 2M Tris-HCl (pH 9.0) and concentrated by Centricon (Amicon). Dialysis against PBS gave TAT-Bcl-xFNK preparation for use in the following experiment. TAT-Bcl-xFNK was prepared from the insoluble fraction (inclusion body) as follows. The harvested cells were washed 3 times with PBS, then suspended in 36 ml of Buffer A (50 mM Tris-HCl pH 8.0, 150 mM NaCl, 1 mM EDTA, 1 mM DTT) containing DTT in place of PMSF, and disrupted by ultracentrifugation. Triton X-100 (final concentration 1%) was added, and the mixture was placed on ice for 10 minutes. The inclusion body containing TAT-Bcl-xFNK was precipitated by centrifugation, and washed twice with Buffer A containing Triton X-100. Finally, the inclusion body was solubilized in PBS containing 7M urea and 1 mM DTT. This preparation was confirmed to contain TAT-Bcl-xFNK protein of 70% purity by SDS-polyacrylamide gel electrophoresis and used in the following experiment.

Example 10

Incorporation of TAT-Bcl-xFNK Protein in Cells

TAT-Bcl-xFNK protein (1 μM) was added to DMEM/F-12 (Life Technologies) containing 10% FBS (fetal bovine serum), a medium for HeLa cells cultured in a Slide Chamber (Lab-Tek), and the cells were incubated in a $CO_2$ incubator for 24 hours. The cells were then washed twice with PBS. The cells were fixed with paraformaldehyde (4%) dissolved in PBS at room temperature for 45 min. The cells were washed 3 times with PBS (5 minutes/round), and incubated in PBS containing 10% FBS for 20 min. The cells were washed 3 times with PBS (5 minutes/round), and treated with 1.5% FBS-PBS solution containing an anti-rat Bcl-$x_L$ monoclonal antibody 35-32 (murine origin) for 30 min. The cells were washed 3 times with PBS (5 minutes/round), and treated with 1.5% FBS-PBS solution containing an anti-mouse IgG antibody conjugated with FITC, for 30 minutes. The cells were washed 3 times with PBS (5 minutes/round), mounted in PBS, and sealed to observe under a fluorescence microscope.

Figure 18:
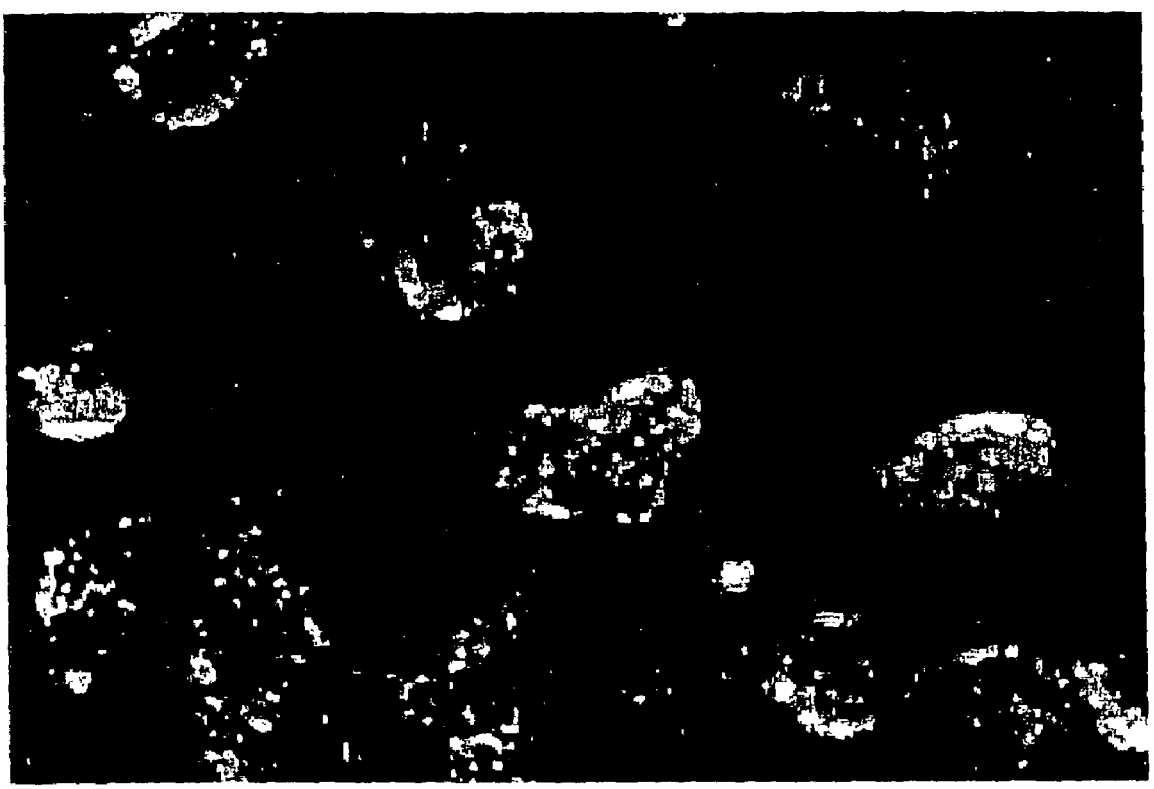
FIG. 18 is a microscopic photograph showing a state of the protein TAT-Bcl-xFNK incorporated in the HeLa cells.
Figure 19:
FIG. 19 is a microscopic photograph of the chondrocytes in cartilage slice incubated in a culture medium containing the protein TAT-Bcl-xFNK for 5 days.
Figure 20:
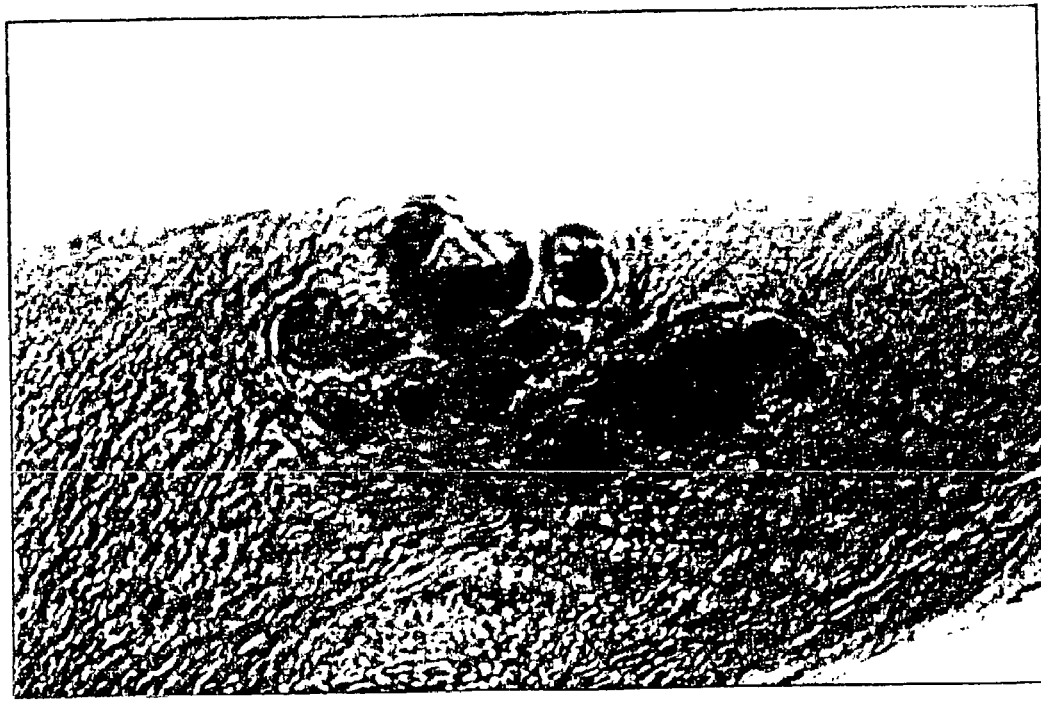
FIG. 20 is a microscopic photograph of the chondrocytes in cartilage slice incubated in a culture medium containing the protein TAT-Bcl-xFNK for 9 days.
Figure 21:
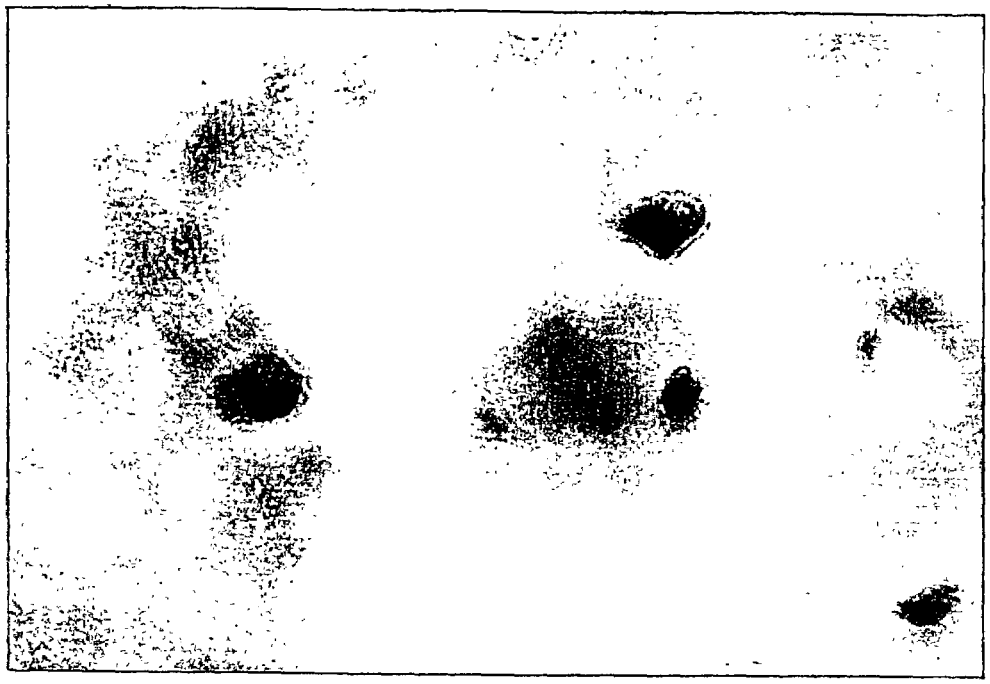
FIG. 21 is a microscopic photograph of the chondrocytes in cartilage slice incubated in a culture medium containing the protein TAT-Bcl-$x_L$ for 5 days.
Figure 22:
FIG. 22 is a microscopic photograph of the chondrocytes in cartilage slice incubated in a culture medium containing the protein TAT-Bcl-$x_L$ for 9 days.
Figure 23:
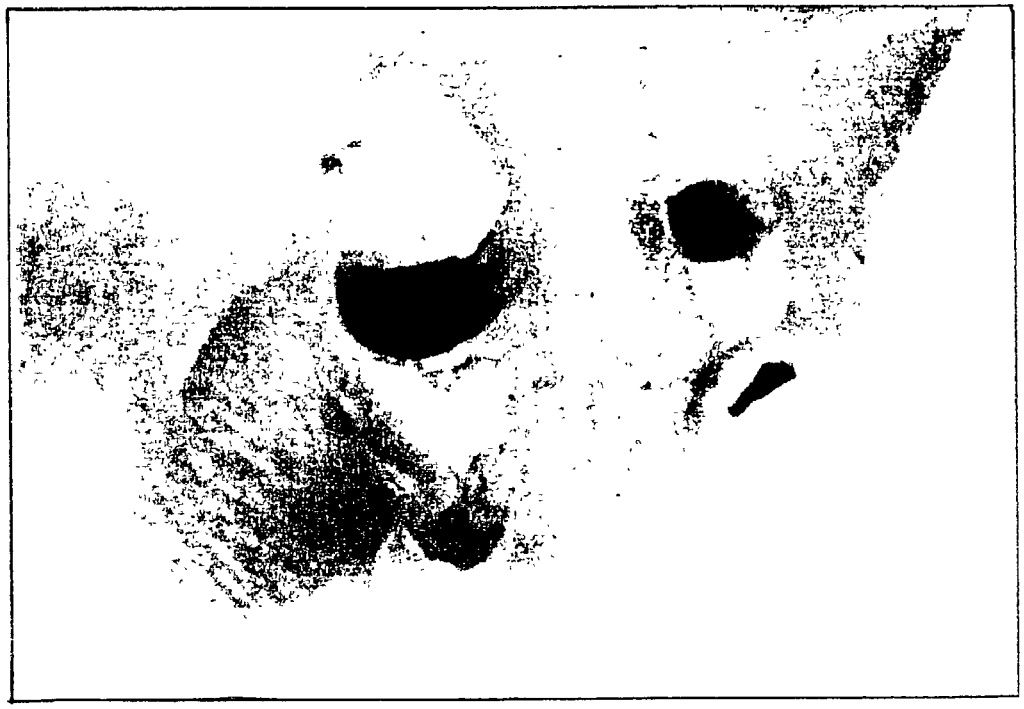
FIG. 23 is a microscopic photograph of the chondrocytes in cartilage slice incubated in a culture medium containing a solvent (PBS) for 5 days.
Figure 24:
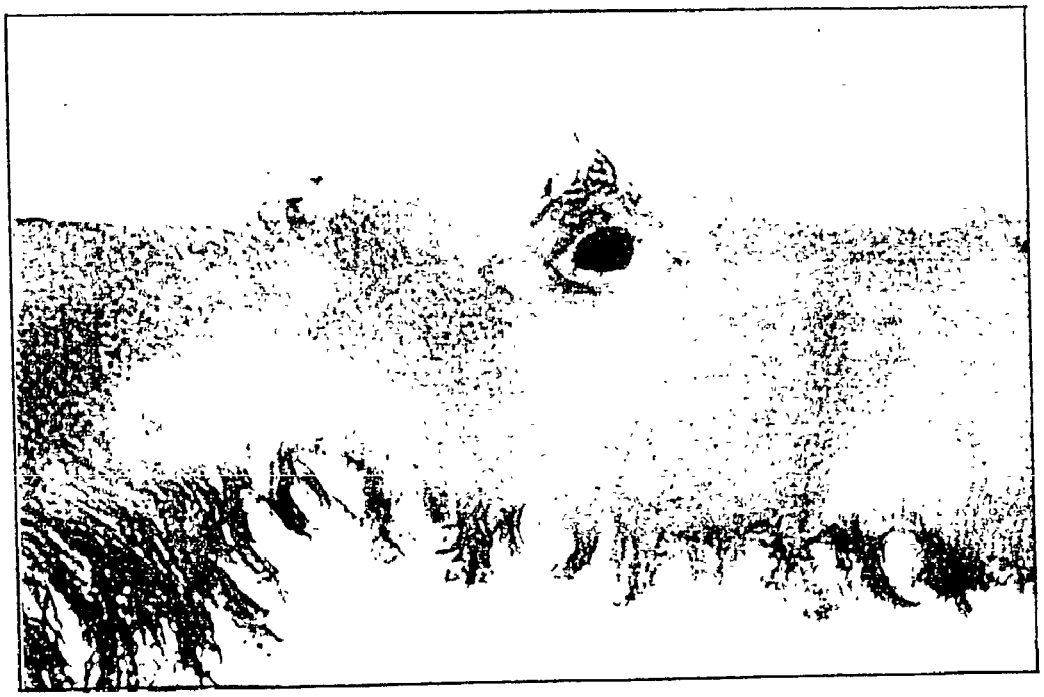
FIG. 24 is a microscopic photograph of the chondrocytes in cartilage slice incubated in a culture medium containing a solvent (PBS) for 9 days.

The results are shown in FIG. 18. Spotted fluorescence characteristic to FITC was observed in the cells. This fluorescence signal could not be observed in the cells incubated without TAT-Bcl-xFNK protein. Further, even though the TAT-Bcl-xFNK protein was added, when the cells were not treated with the primary antibody (35-32), no signal was observed. These results indicate that the TAT-Bcl-xFNK protein added to the culture medium has passed through the cellular membrane and has been incorporated in the cells.

Example 11

Introduction of Tat-Bcl-xFNK into the Chondrocyte of Cartilage Slice Culture and Confirmation of the Cell Death-Inhibiting Activity Cartilage was obtained from the femoral bone head of Osteoarthritis patients undergoing total hip arthroplasty. The cartilage tissue above the subchondral bone (10×10 mm; 1.2 mm in thickness) was aseptically sliced using a single-edged razor. The cartilage slice was placed in a 24-well plate and incubated with an DMEM/Ham F-12 mixed medium (Life Technologies) containing 20% FBS (fetal bovine serum) at 37° C. in a $CO_2$ incubator. For a comparative experiment, the expression vector of TAT-Bcl-$x_L$ was constructed in the same manner as TAT-Bcl-xFNK, and TAT-Bcl-$x_L$ protein was partially purified from *Escherichia coli* (TAT-Bcl-$x_L$ preparation has the same purity). TAT-Bcl-xFNK (prepared from the inclusion body) or TAT-Bcl-$x_L$ (prepared from the inclusion body) were added to the culture medium at a concentration of 0.2 μM. As a control, an equal amount of PBS (a solvent used to solubilize the proteins) containing 7M urea and 1 mM DTT was added. The culture medium containing the protein was changed on day 4 and day 7. After incubation for 4 days and 9 days, the cartilage slice was frozen to prepare frozen sections using a cryostat. The sections were stained with hematoxylin-eosin to evaluate the death of chondrocyte. As shown in FIGS. 19 to 24, the results indicate that TAT-Bcl-xFNK inhibits the death of chondrocyte more strongly than TAT-Bcl-$x_L$, and the difference between them is more remarkable on day 9. It was shown that TAT-Bcl-xFNK protein in the culture medium was incorporated into the chondrocytes buried in the cartilage tissue to exhibit its powerful activity to inhibit cell death.

Example 12

Figure 25:
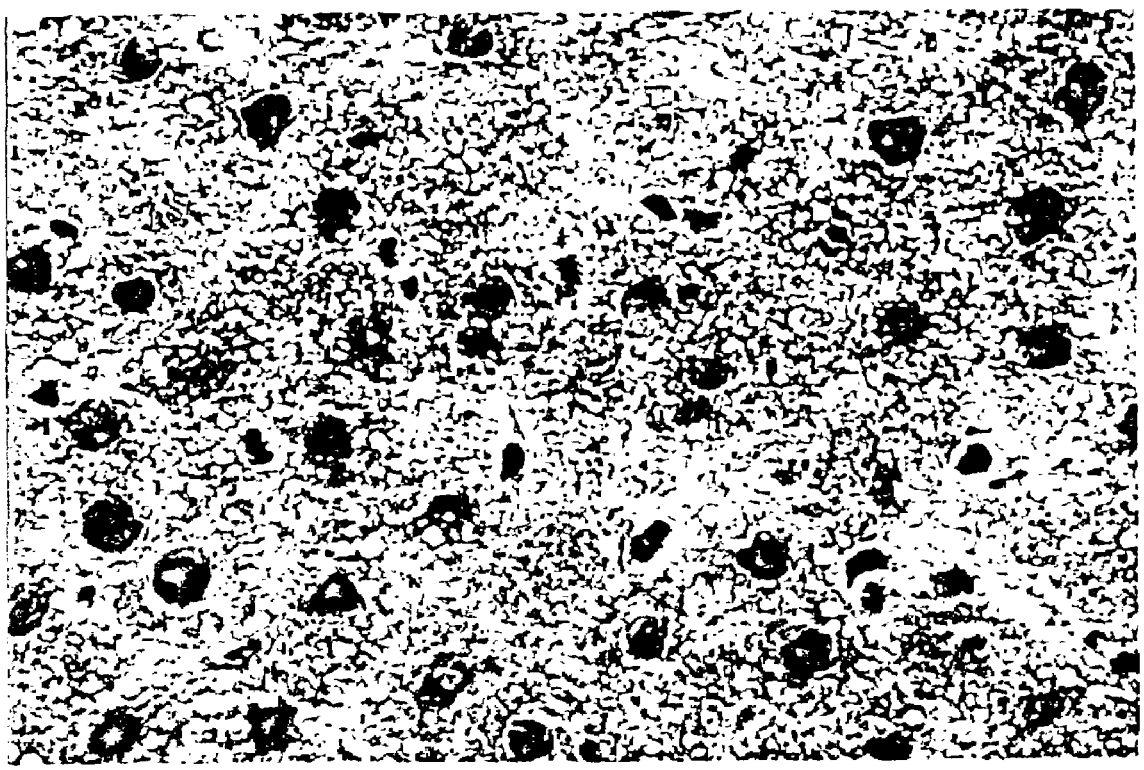
FIG. 25 is a microscopic photograph showing the liver slice of a mouse to which the protein TAT-Bcl-xFNK has been administered systemically, followed by administration of dexamethasone.
Figure 26:
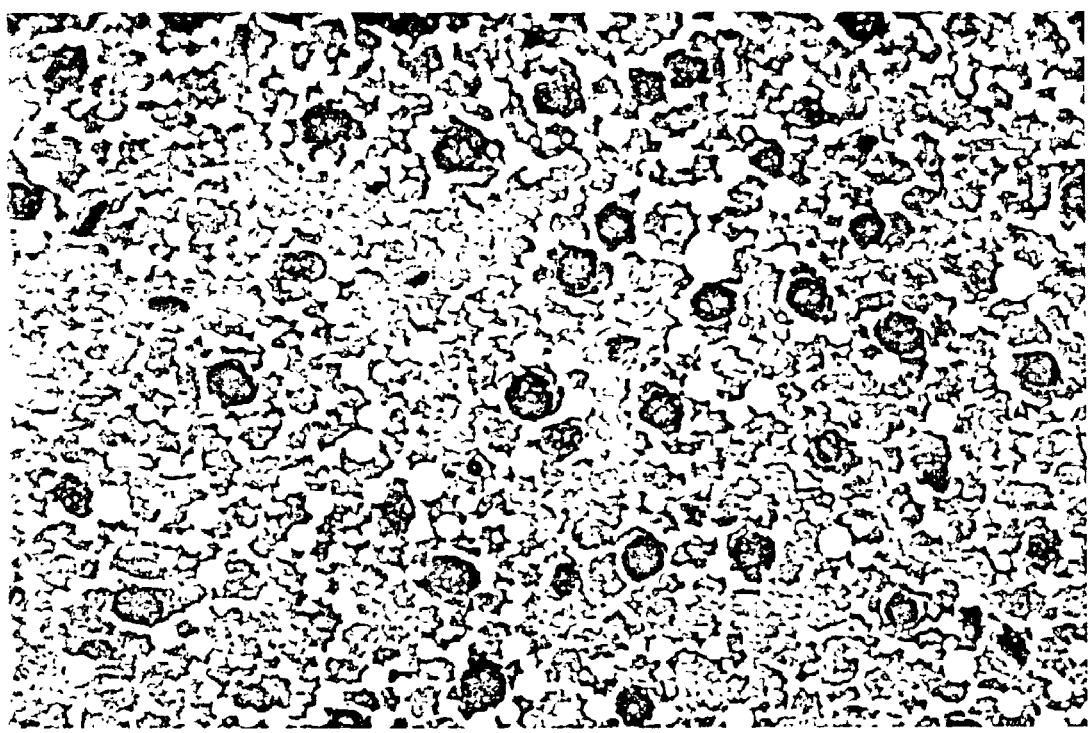
FIG. 26 is a microscopic photograph showing the liver slice of a mouse to which a solvent (PBS) has been administered systemically, followed by administration of dexamethasone.
Figure 27:
FIG. 27 is a microscopic photograph showing the liver slice of a mouse to which a solvent (PBS) only has been administered systemically.

Administration of Tat-Bcl-xFNK to Mice and Confirmation of the Inhibition of the Death of Hepatocytes Caused by Steroid Hormone Three 8-week old mice (C56BL, 20 g body weight, female) were divided into 3 groups (A, B and C). To the mouse of Group A was intraperitonealy administered PBS solution (0.8 ml) containing 100 μg of TAT-Bcl-xFNK protein (prepared from the soluble fraction). To the mice of Group B and Group C (control) was intraperitonealy administered PBS (0.8 ml) in the same manner. The mice were put back into cages, and after a lapse of 3 hours 0.5 ml of 25% ethanol/PBS solution containing 0.5 mg of a steroid hormone (dexamethasone) was intraperitonealy administered to the mice of Group A and Group B. To the mouse of Group C was intraperitonealy administered 0.5 ml of 25% ethanol/PBS solution. They were put back into cages, and after a lapse of 3 hours killed. Their livers were taken out, and frozen to prepare frozen sections with a cryostat. The sections were stained with hematoxylin-eosin to evaluate the death of hepatocyte. Degeneration of the hepatic tissue and cell death caused by dexamethasone in Group B as shown in FIG. 26 were markedly inhibited by pre-administration of TAT-Bcl-xFNK (Group A; FIG. 25). The degree was shown to be better than that of the control (Group C; FIG. 27).

The above results indicate that the protein TAT-Bcl-xFNK intraperitoneally administered is delivered into the hepatic cells to strongly inhibit cell death caused by dexamethasone.

As described above in detail, the invention of the present application provides a engineered cDNA producing an improved protein of rat Bcl-$x_L$ which exhibits the more enhanced activity to inhibit cell death, a recombinant vector having the engineered cDNA, and cells transfected with the recombinant vectors. The transfected cells can be proliferated in a serum-free medium, and are useful for, for example, cell culture systems to efficiently produce useful substances such as physiologically active substances, monoclonal antibodies, and the like. Moreover, the invention of the present application provides an improved protein of rat Bcl-$x_L$ which exhibits the more enhanced activity to inhibit cell death. The improved protein, when it has a protein-transduction-domain peptide, is incorporated into cells and transiently present in the cells to inhibit apoptosis/cell death. The protein is, accordingly, useful as, for example, an ingredient for remedies for various diseases accompanied with cell death or for additives for stably maintaining trans-planted cells or organs.

What is claimed is:

1. A genetically engineered cDNA of the rat bcl-x gene, which comprises the nucleotide sequence of SEQ ID NO: 1 except having at least one nucleotide substitution which changes, in the amino acid sequence encoded by SEQ ID NO: 1, tyrosine (Tyr) at amino acid residue 22 to phenylalanine (Phe), glutamine (Gln) at amino acid residue 26 to asparagine (Asn), and arginine (Arg) at amino acid residue 165 to lysine (Lys).

2. The genetically engineered cDNA of claim 1, which is attached at its 5'-end with an oligonucleotide encoding a protein-transduction-domain peptide.

3. The genetically engineered cDNA of claim 2, wherein the oligonucleotide encodes the amino acid sequence of SEQ ID NO: 12 or 13.

4. A recombinant vector comprising the genetically engineered cDNA of claim 1.

5. An isolated cell comprising the recombinant vector of claim 4.

6. A recombinant vector comprising the genetically engineered cDNA of claim 2.

7. A recombinant vector comprising the genetically engineered cDNA of claim 3.

8. An isolated cell comprising the recombinant vector of claim 6.

9. An isolated cell comprising the recombinant vector of claim 7.

10. An isolated polynucleotide comprising the nucleotide sequence of SEQ ID NO: 1 except having at least one nucleotide substitution which changes, in the amino acid sequence encoded by SEQ ID NO: 1, tyrosine (Tyr) at amino acid residue 22 to phenylalanine (Phe), glutamine (Gln) at amino acid residue 26 to asparagine (Asn), arginine (Arg) at amino acid residue 165 to lysine (Lys), or a combination thereof.

11. The polynucleotide of claim 10, which is attached at its 5'-end with an oligonucleotide encoding a protein-transduction-domain peptide.

12. The polynucleotide of claim 11, wherein the oligonucleotide encodes the amino acid sequence of SEQ ID NO: 12 or 13.

13. A recombinant vector comprising the polynucleotide of claim 10.

14. An isolated cell comprising the recombinant vector of claim 13.

15. A recombinant vector comprising the polynucleotide of claim 11.

16. A recombinant vector comprising the polynucleotide of claim 12.

17. An isolated cell comprising the recombinant vector of claim 15.

18. An isolated cell comprising the recombinant vector of claim 16.

19. The genetically engineered cDNA of claim 1, which expresses a polypeptide comprising the amino acid sequence of SEQ ID NO: 2, and having at least one amino acid substitution selected from the group consisting of substitution of Tyr at amino acid residue 22 to Phe, substitution of Gln at amino acid residue 26 to Asn and substitution of Arg at amino acid residue 165 to Lys.

20. The isolated polynucleotide of claim 10, which encodes a polypeptide comprising the amino acid sequence of SEQ ID NO: 2, and having at least one amino acid substitution selected from the group consisting of substitution of Tyr at amino acid residue 22 to Phe, substitution of Gln at amino acid residue 26 to Asn and substitution of Arg at amino acid residue 165 to Lys.

* * * * *